United States Patent
Kozuka et al.

(10) Patent No.: US 9,111,027 B2
(45) Date of Patent: Aug. 18, 2015

(54) SIMILAR CASE SEARCH APPARATUS AND SIMILAR CASE SEARCH METHOD

(71) Applicant: PANASONIC CORPORATION, Osaka (JP)

(72) Inventors: Kazuki Kozuka, Osaka (JP); Kazutoyo Takata, Osaka (JP); Takashi Tsuzuki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 477 days.

(21) Appl. No.: 13/657,240

(22) Filed: Oct. 22, 2012

(65) Prior Publication Data

US 2013/0044925 A1 Feb. 21, 2013

Related U.S. Application Data

(63) Continuation of application No. PCT/JP2012/000885, filed on Feb. 9, 2012.

(30) Foreign Application Priority Data

Feb. 14, 2011 (JP) .................................. 2011-029169

(51) Int. Cl.
*G06K 9/00* (2006.01)
*G06F 19/00* (2011.01)
(Continued)

(52) U.S. Cl.
CPC ............ *G06F 19/3443* (2013.01); *G06Q 10/06* (2013.01); *G06Q 10/10* (2013.01); *G06Q 50/24* (2013.01)

(58) Field of Classification Search
None
See application file for complete search history.

(56) References Cited

U.S. PATENT DOCUMENTS

2009/0132499 A1  5/2009  Yamagishi et al.
2010/0274776 A1  10/2010  Iizuka
2011/0099032 A1  4/2011  Miyasa et al.

FOREIGN PATENT DOCUMENTS

JP  2004-157623  6/2004
JP  2009-78085   4/2009
(Continued)

OTHER PUBLICATIONS

International Search Report issued Apr. 24, 2012 in International Application No. PCT/JP2012/000885.
(Continued)

*Primary Examiner* — Stephen R Koziol
*Assistant Examiner* — Raphael Schwartz
(74) *Attorney, Agent, or Firm* — Wenderoth, Lind & Ponack, L.L.P.

(57) ABSTRACT

A similar case search apparatus includes: a keyword extracting unit which extracts a keyword from an image interpretation report; a diagnosis tree analyzing unit which extracts, based on the keyword, one or more target diagnosis flows corresponding to the image interpretation report, by referring to a diagnosis tree storage unit storing diagnosis trees; a similar diagnosis flow extracting unit which extracts one or more diagnosis flows similar to the one or more target diagnosis flows from among the plurality of diagnosis flows included in the diagnosis trees stored in the diagnosis tree storage unit, based on the degree of difficulty regarding a diagnosis item or the degree of difficulty regarding a disease name; and a similar case searching unit which searches out one or more case data sets corresponding to the similar diagnosis flows from among a plurality of case data sets stored in a case data storage unit.

8 Claims, 27 Drawing Sheets

(51) Int. Cl.
*G06Q 10/06* (2012.01)
*G06Q 10/10* (2012.01)
*G06Q 50/24* (2012.01)

(56) References Cited

FOREIGN PATENT DOCUMENTS

| JP | 2009-129108 | 6/2009 |
| JP | 2010-79568 | 4/2010 |
| JP | 2011-92286 | 5/2011 |

OTHER PUBLICATIONS

Kazuya Okamoto et al., "Context-based Retrieval System for Similar Medical Practice Documents", Transactions of the Japanese Society for Medical and Biological Engineering, vol. 44(1), pp. 199-206, Mar. 10, 2006 (with English abstract).

FIG. 2

| Test Report | | | |
|---|---|---|---|
| | | | Month Date, Year |
| Date of test | Month Date, Year | Date of entry | Month Date, Year |
| ID | 0001 | Name | ■ ■ |
| Medical department | Internal medicine | Hospital name | XX hospital |
| Birthday | January 1st, 1960 | Test area | Abdominal CT Liver |
| Age | 50 years old | Sex | M |
| Contrast medium | Gd-DTPA | Film | Findings |

Findings

<Diagnosis item 1> is <Diagnosis result (state) A>.
<Diagnosis item 2> is <Diagnosis result (state) B>.
<Diagnosis item 3> is <Diagnosis result (state) C>.

(Example: Tumor border part is clear and smooth)

Disease name

<Disease name> is suspected.

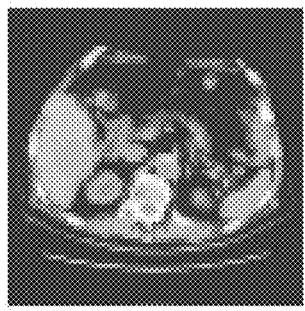 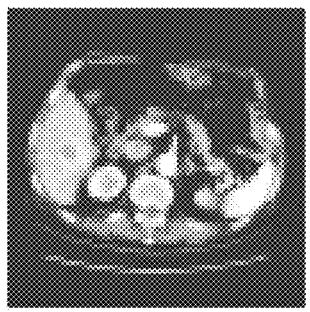 ... 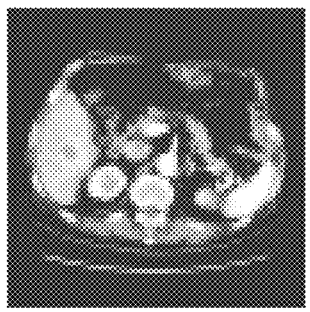

ID: 0001          ID: 0001          ID: 0001
CT image 1        CT image 2        CT image 100

FIG. 26

Experimental result (conventional method: similarity evaluation based on the number of matching character strings)

| Rank | Similarity | Diagnosis flow (Diagnosis / Disease name) | | | | Disease name |
|---|---|---|---|---|---|---|
| | | Diagnosis item 1 | Diagnosis result 1 | Diagnosis item 2 | Diagnosis result 2 | |
| 1 | 1.0 | a | B | c | G | S |
| 2 | 0.8 | a | B | c | G | T |
| 2 | 0.8 | a | B | c | G | U |
| 2 | 0.8 | a | B | c | H | S |
| 2 | 0.8 | a | B | c | I | S |
| 6 | 0.6 | a | B | c | H | V |
| 6 | 0.6 | a | B | c | H | T |
| 6 | 0.6 | a | B | c | I | W |
| 9 | 0.4 | a | C | d | K | S |
| 10 | 0.2 | a | Others | | | |

FIG. 27

Test result (proposed method: similarity evaluation based on diagnostic difficulty)

| Rank | Similarity | Diagnosis flow (Diagnosis / Disease name) | | | | Disease name |
|---|---|---|---|---|---|---|
| | | Diagnosis item 1 | Diagnosis result 1 | Diagnosis item 2 | Diagnosis result 2 | |
| 1 | 1.0 | a | B | c | G | S |
| 2 | 0.9 | a | B | c | H | S |
| 2 | 0.9 | a | B | c | I | S |
| 4 | 0.8 | a | B | c | G | T |
| 4 | 0.8 | a | B | c | G | U |
| 6 | 0.7 | a | B | c | H | V |
| 6 | 0.7 | a | B | c | H | T |
| 6 | 0.7 | a | B | c | I | W |
| 9 | 0.5 | a | C | d | K | S |
| 10 | 0.3 | Other combinations | | | | |

FIG. 28

Test result (proposed method: similarity evaluation based on diagnostic difficulty)

| Rank | Similarity | Diagnosis flow (Diagnosis / Disease name) | | | | Disease name |
|---|---|---|---|---|---|---|
| | | Diagnosis item 1 | Diagnosis result 1 | Diagnosis item 2 | Diagnosis result 2 | |
| 1 | 1.0 | a | B | c | G | S |
| 2 | 0.9 | a | B | c | G | T |
| 2 | 0.9 | a | B | c | H | S |
| 2 | 0.9 | a | B | c | H | T |
| 5 | 0.8 | a | B | c | I | S |
| 5 | 0.8 | a | B | c | G | U |
| 7 | 0.7 | a | B | c | H | V |
| 8 | 0.6 | a | B | c | I | W |
| 9 | 0.5 | a | C | d | K | S |
| 9 | 0.5 | a | C | d | K | T |

FIG. 29

Test result (proposed method: similarity evaluation based on diagnostic difficulty)

| Rank | Similarity | Diagnosis flow (Diagnosis / Disease name) | | | | |
|---|---|---|---|---|---|---|
| | | Diagnosis item 1 | Diagnosis result 1 | Diagnosis item 2 | Diagnosis result 2 | Disease name |
| 1 | 1.0 | a | B | c | G | S |
| 2 | 0.9 | a | B | c | H | T |
| 2 | 0.9 | a | B | c | I | S |
| 2 | 0.9 | a | B | c | G | T |
| 2 | 0.9 | a | B | c | H | S |
| 6 | 0.8 | a | B | c | G | U |
| 7 | 0.7 | a | B | c | H | V |
| 7 | 0.7 | a | B | c | I | W |
| 9 | 0.5 | a | C | d | K | S |
| 10 | 0.4 | a | C | d | K | T |

SIMILAR CASE SEARCH APPARATUS AND SIMILAR CASE SEARCH METHOD

CROSS REFERENCE TO RELATED APPLICATIONS

This is a continuation application of PCT Patent Application No. PCT/JP2012/000885 filed on Feb. 9, 2012, designating the United States of America, which is based on and claims priority of Japanese Patent Application No. 2011-029169 filed on Feb. 14, 2011. The entire disclosures of the above-identified applications, including the specifications, drawings and claims are incorporated herein by reference in their entirety.

FIELD

One exemplary embodiment disclosed herein relates to a similar case search apparatus and a similar case search method for searching out a case data set similar to data in a target image interpretation report from a case database storing case data sets each including medical images and an image interpolation report of the medical images.

BACKGROUND

Recently, medical images previously interpreted to make diagnoses and information related to the results of the image interpretations and the results of the diagnoses are actively stored in databases for the purposes of helping radiologists to interpret medical images and helping clinicians to make diagnoses. Furthermore, similar case search systems have been proposed which are intended to search out, from the databases, medical images similar to target medical images to be interpreted by doctors to make diagnoses and the information related to the results of interpreting the medical images and the results of the diagnoses.

In such a conventional similar case search system, a database stores a large number of document data sets (hereinafter referred to as "image interpretation reports") related to the results of image interpretations and diagnoses. In this case, the database is searched for image interpretation reports including character strings (words) similar to character strings included in an image interpretation report (hereinafter referred to as a "current image interpretation report") input by a doctor. As a result, the searched-out similar image interpretation report and the medical images associated with the similar image interpretation report are output as the result of the search (see Non-patent Literature (NPL) 1).

In such a conventional case search system, the image interpretation report is searched out using a vector having, as an element, the total number of keywords included in the image interpretation report. More specifically, the degree of similarity of each image interpretation report in the database with respect to a current image interpretation report is calculated by calculating the distance between the vector of the image interpretation report in the database and the vector of the current image interpretation report. In the search, image interpretation reports found to have a higher similarity are preferentially searched out.

CITATION LIST

Non Patent Literature

Context-based Retrieval System for Similar Medical Practice Documents, (Medical and Biological Engineering 44(1): 199-206, 2006)

SUMMARY

Technical Problem

According to the aforementioned conventional case search system, it is possible to search out an image interpretation report having a high matching rate in character strings with a current image interpretation report, as an image interpretation report similar to the current image interpretation report.

However, when a doctor is provided with a case data set including an image interpretation report having a high matching rate in character strings with the current image interpretation report, the doctor cannot determine the degree of medical similarity of the case data set with respect to a current case to be diagnosed. For this reason, the doctor is highly likely to have difficulty in determining the disease name. In such a case, the doctor makes a diagnosis based on the states described in the current image interpretation report by using a plurality of case data sets searched out based on search keywords other than the keywords included in the current image interpretation report. In other words, in some cases, the conventional method does not make it possible to search out appropriate case data sets from among a plurality of case data sets.

One non-limiting and exemplary embodiment provides a similar case search apparatus which makes it possible to search out appropriate case data sets from among a plurality of case data sets.

Solution to Problem

A similar case search apparatus according to an aspect of the present invention includes: a keyword extracting unit configured to extract a keyword from an image interpretation report that is document data including a diagnosis item and a diagnosis result, the diagnosis item being a diagnosis target in interpretation of a medical image, and the diagnosis result showing a state of the diagnosis item; a diagnosis tree analyzing unit configured to extract, based on the keyword, one or more target diagnosis flows corresponding to the image interpretation report, by referring to a diagnosis tree storage unit storing one or more diagnosis trees each of which includes a plurality of diagnosis flows each including a diagnosis item and a state of the diagnosis item which are used to determine a disease name; a similar diagnosis flow extracting unit configured to extract one or more similar diagnosis flows similar to the one or more target diagnosis flows from among the plurality of diagnosis flows included in the diagnosis trees stored in the diagnosis tree storage unit, based on a degree of difficulty regarding a diagnosis item or a degree of difficulty regarding a disease name, the degree of difficulty regarding a diagnosis item being a degree of difficulty in determining a state of a diagnosis item, and the degree of difficulty regarding a disease name being a degree of difficulty in determining a disease name; and a similar case search unit configured to search out one or more case data sets corresponding to the one or more similar diagnosis flows from among a plurality of case data sets stored in a case data storage unit.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

A similar case search apparatus according to an aspect of the present disclosure makes it possible to search out appropriate case data sets from among a plurality of case data sets.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 2 shows examples of a test report (an image interpretation report) and medical images.

FIG. 26 is a table showing the result of a similar case search experiment.

FIG. 27 is a table showing the result of a similar case search experiment.

FIG. 28 is a table showing the result of a similar case search experiment.

FIG. 29 is a table showing the result of a similar case search experiment.

DESCRIPTION OF EMBODIMENT (Underlying Knowledge Forming Basis of the Present Disclosure)

Figure 1:
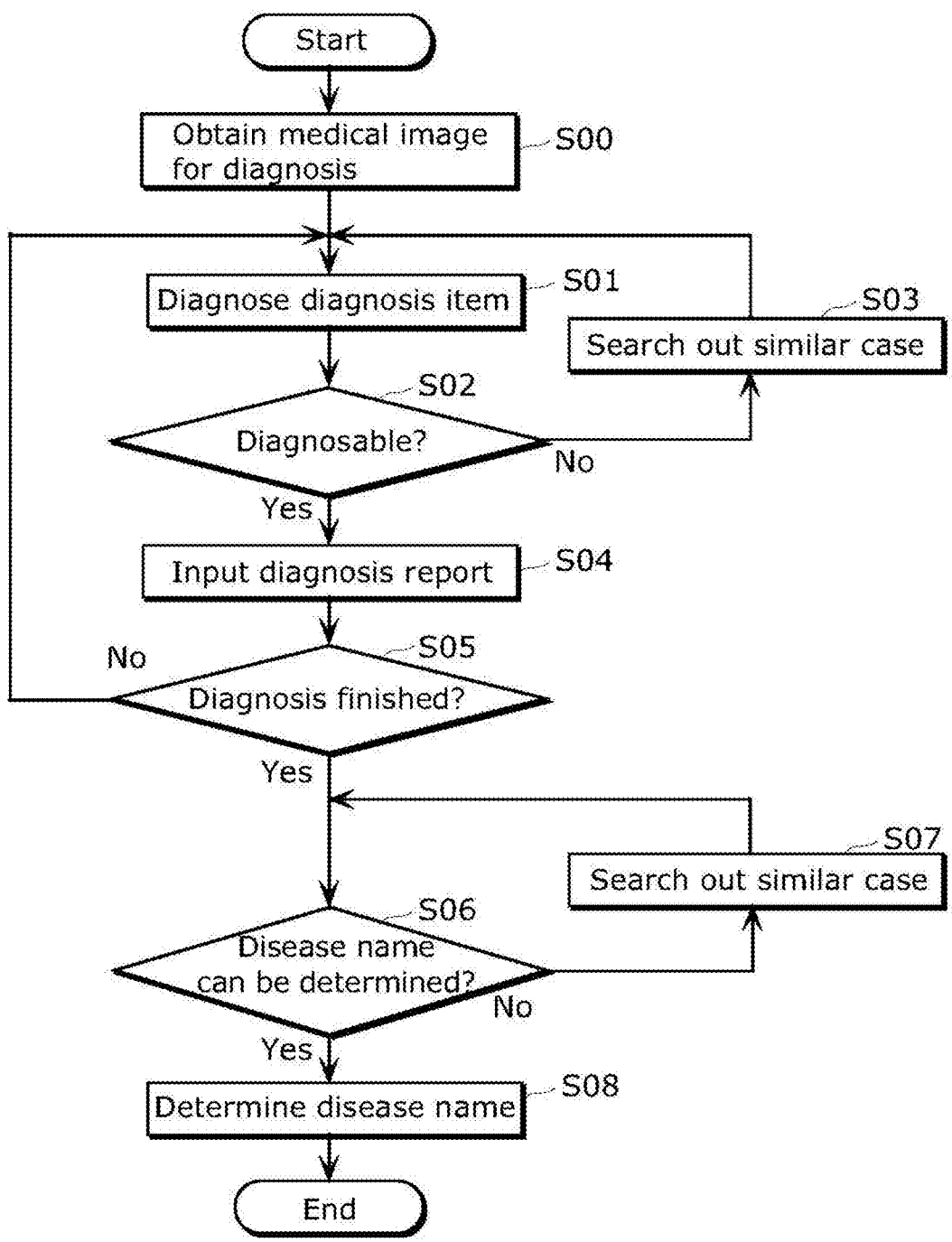
FIG. 1 is a flowchart of a medical image interpretation procedure taken by a doctor.

First, a general medical image interpretation procedure take by a doctor is described briefly with reference to FIG. 1 and FIG. 2, before explaining a similar case search apparatus according to an aspect of the present disclosure. FIG. 1 is a flowchart of a medical image interpretation procedure taken by a doctor. FIG. 2 is a diagram of an exemplary set of medical images and the image interpretation report of the medical images.

Terms to be used here are described briefly. The term "diagnosis item" refers to the area or kind of a lesion that is a diagnosis target in the interpretation of a medical image. The term "state" refers to a condition of the lesion or the lesion area. In addition, the term "the result of a diagnosis" refers to the state of the diagnosis item obtained by a doctor's diagnosis of or based on the diagnosis item.

In addition, the term "image interpretation report" refers to a document data set of a diagnosis item and a diagnosis result of the diagnosis item. For example, when an image interpretation report includes a description that "the tumor border part is clear and smooth", the diagnosis item is a "tumor border part", and the diagnosis result is "clear and smooth".

In addition, the term "disease name" refers to the name of a disease that is finally determined by a doctor based on the diagnosis result of each of diagnosis items. In addition, the term a "case data set" refers to a data set including medical images and the image interpretation report of the medical images.

Hereinafter, a diagnosis procedure taken by a doctor is described with reference to FIG. 1.

First, the doctor obtains a medical image to be interpreted for making a diagnosis (such as an medical image obtained by, for example, computer tomography (CT) or magnetic resonance imaging (MRI)) (S00).

Next, the doctor interprets the medical image and diagnoses the diagnosis item (S01).

Here, when the doctor cannot determine the state of the diagnosis item (No in S02), the doctor searches out the diagnosis item and diagnosis result associated with a medical image previously interpreted and similar to the diagnosis item and diagnosis result associated with a medical image that is currently being interpreted (S03), and diagnoses the diagnosis item by utilizing the searched-out results (S01).

On the other hand, when the doctor can determine the state of the diagnosis item (Yes in S02), the doctor inputs the diagnosis item and the diagnosis result in a Findings column as shown in FIG. 2.

Here, when the diagnosis of any diagnosis item necessary to determine a disease name is not yet completed (No in S05), the doctor returns to Step S01 and then diagnoses the next diagnosis item.

On the other hand, when the diagnoses of all diagnosis item necessary to determine a disease name is already completed (Yes in S05), the doctor judges whether it is possible to determine the disease name (S06).

Here, it is impossible to determine the disease name (No in S06), the doctor searches out past case data sets (hereinafter referred to as "similar case data sets") similar in the diagnosis items and diagnosis results to the current case data set including interpretation target medical images (S07), and judges whether or not it is possible to determine the disease name by utilizing the searched-out results.

On the other hand, when it is possible to determine the disease name (Yes in S06), the doctor determines the disease name based on the diagnosis result of the diagnosis item (S08). Next, the doctor inputs the determined disease name in a Disease name column as shown in FIG. 2.

The doctor interprets the medical images according to a procedure as described above. At this time, the doctor searches out a similar case if he or she cannot confidently diagnose the diagnosis item or determine the disease name. Next, the doctor compares the searched-out similar case with the current medical image, which enables the doctor to obtain a clue for diagnosing the diagnosis item or determining the disease name.

Here, a search of a similar case is considered more specifically. According to the aforementioned image interpretation procedure, a similar case is searched out in each of Steps S03 and S07. More specifically, since, in Step S02, a determination is made as to whether or not it is possible to determine the state of the diagnosis item, the similar case search in Step S03 shows that the doctor cannot confidently diagnose the diagnosis item. On the other hand, since, in Step S06, a determination is made as to whether or not it is possible to determine the name of the disease, the similar case search in Step S07 shows that the doctor cannot confidently determine the disease name. The result of analyzing doctor's states in the image interpretation procedure shows that the states and causes requiring the doctor to search out a similar case are mainly classified into the following five categories.

Hereinafter, the five-category causes are described in detail.

(1) There are highly similar states that are possible as the state of a target diagnosis item to be diagnosed by a doctor.

In this case, the doctor has difficulty in differentiating the states and determining the actual state. As a result, a similar case search is highly likely to be required.

(2) There is a large number of states that are possible as the state of a target diagnosis item to be diagnosed by a doctor.

In this case, the doctor is highly likely to have difficulty in determining the actual state. As a result, a similar case search is highly likely to be required.

(3) There is a large number of diagnosis items required to be diagnosed for the determination of a disease name.

In this case, the determination of the disease name becomes more difficult in proportion to the total number of diagnosis items. As a result, a similar case search is highly likely to be required.

(4) It is impossible to determine a disease name even after diagnosing all diagnosis items required to be diagnosed for the determination of the disease name.

The doctor diagnoses diagnosis items sequentially to finally determine the disease name. There is a case where the doctor cannot narrow down to the disease name even when the diagnoses of all the diagnosis items are completed without leaving any diagnosis item to be diagnosed. In other words, there is a case where plural possible disease names remain even after the diagnoses of all the diagnosis items are completed. In such a case, the doctor has difficulty in determining the disease name. Accordingly, a similar case search is highly likely to be required.

(5) It is impossible to determine a disease name by diagnosing only a single diagnosis item.

The doctor diagnoses various kinds of diagnosis items (the shapes, patterns, etc. of lesions) before determining the disease name. A larger number of kinds of diagnosis items makes the determination of the disease name more difficult, resulting in a higher likelihood that a similar case search is required.

The above-described Categories (1) to (5) are all related to the difficulty in diagnosing the state or determining the disease name. Here, the difficulty shows how much the doctor has difficulty in diagnosing the diagnosis item or determining the disease name. For this reason, it is helpful for doctors to be able to refer to past confusing case data sets presented based on the degrees of difficulty for doctors to diagnose diagnosis items or determine disease names.

More specifically, it is helpful for doctors to be able to not only refer to State A presented in the search of a similar case similar to a case in a current image interpretation report but also refer to case data sets including confusing states (such as States A, D, and G) search out from among states (such as States A, B, C, D, E, F, and G) that are possible as the state of the diagnosis item. At this time, the confusing states (States D and G) are different from State A indicated by one of the character strings in the current image interpretation report based on which the current search is performed, and thus cannot be searched out using a similar case search method based on the degrees of similarity between character strings in image interpretation reports.

In view of this, the Inventors of the present application have considered a similar case search method based not only on the similarity between character strings but also on diagnostic difficulty as described above. Hereinafter, this diagnostic difficulty is referred to as the degrees of diagnostic difficulty or simply as the degrees of difficulty.

Here, the degree of diagnostic difficulty is described more specifically. The degree of diagnostic difficulty shows how much a doctor is confused in making a diagnosis (determining the state and disease name) of or based on the diagnosis item. For example, the degree of difficulty shows how much it is difficult to determine the actual state of a diagnosis item from among State A and State B. In addition, for example, the degree of difficulty shows how much it is difficult to determine the actual disease name from among Disease name C and Disease name D.

Such similar case searches based on the degrees of diagnostic difficulty enable doctors to search out cases that often confuse doctors. However, such past image interpretation reports do not include a description of the degree of difficulty regarding each diagnosis item. In addition, it is difficult to cause doctors to assign the degrees of difficulty to the past cases. Accordingly, the degrees of diagnostic difficulty must be determined based on data or information other than the image interpretation reports.

For this reason, the Inventors of the present application have focused on the relationships between diagnosis procedures taken by doctors and the degrees of diagnostic difficulty. It is possible to search out cases that are diagnostically confusing for a doctor by extracting the degrees of difficulty based on the diagnosis procedure taken for a case to be diagnosed by the doctor. A method of extracting the degrees of difficulty based on the diagnosis procedures is described below.

First, a diagnosis flow is described. A doctor determines the state of each diagnosis item based on medical knowledge. The doctor repeats iterations of the determination on each diagnosis item to finally determine the disease name. The diagnosis flow used here includes one or more possible disease names, diagnosis items to be diagnosed before the disease name or one of the disease names is finally determined, and the states of the diagnosis items.

More specifically, the doctor firstly diagnoses a predetermined diagnosis item. For example, when diagnosing a mamma using an ultrasound, a doctor firstly determines the state of a border part (from among "clear and smooth", "clear and irregular", or "unclear"). Next, the doctor diagnoses the next diagnosis item depending on the result of diagnosing the border part. For example, when the border part is "clear and smooth", the doctor makes a diagnosis based on the shape of the border part next. When the border part is "clear and irregular" or "unclear", the doctor makes a diagnosis as to whether there is a tear in the border part next. In other words, the doctor diagnoses the diagnosis items that are determined depending on the result(s) of diagnosing the previous diagnosis item(s) to finally determine the disease name.

For this reason, diagnosis flows can be represented in the form of a tree in which the diagnosis items and the states thereof are combined with each other. In addition, each of the diagnosis flows can be determined previously to some extent depending on the test area and the kinds of medical images. Accordingly, this tree can be formed based on medical books, past cases, etc. Hereinafter, a set of such diagnosis flows represented in the form of a tree is referred to as a diagnosis tree.

Figure 3:
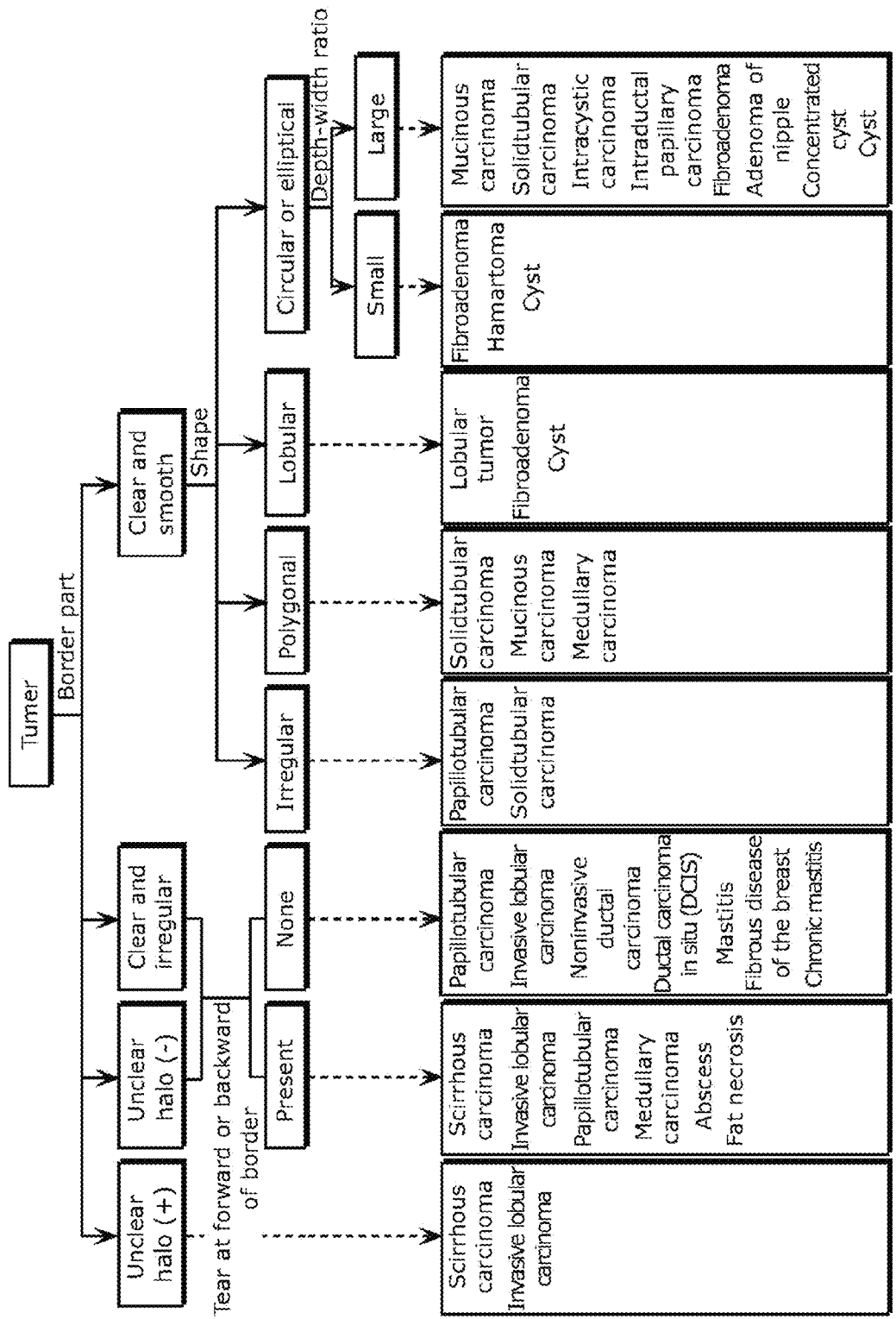
FIG. 3 shows an exemplary diagnosis tree.

In general, doctors determine a disease name by making diagnoses from various angles instead of determining a disease name based only on a single diagnosis tree. For this reason, in most cases, the doctors diagnose by using, in combination, several kinds of diagnosis trees (such as a diagnostic tree of shapes and a diagnostic tree of texture) for a diagnosis target. Here, FIG. 3 shows an exemplary diagnosis tree of shapes in a diagnosis of a mamma using an ultrasound.

The diagnosis tree has information regarding diagnosis items, the different states of the diagnosis items, and possible disease names. As mentioned above, the diagnosis tree includes a plurality of diagnosis flows. With reference to the diagnosis tree, it is possible to determine one of the diagnosis flows based on the diagnosis items, the diagnosis results, and the disease names described in a current image interpretation report. In addition, it is possible to find which part of the diagnosis tree corresponds to the diagnosis flow described in the image interpretation report.

The diagnosis tree includes information about the diagnosis items, the different states, and the disease names. Thus, it is possible to calculate, for the respective causes requiring a similar case search, the degrees of diagnostic difficulty determined based on the information about branches in the tree and the total number of the branches. The degrees of difficulty are calculated based on indicators described below.

Evaluation Indicator Regarding Item (1)

Figure 4:
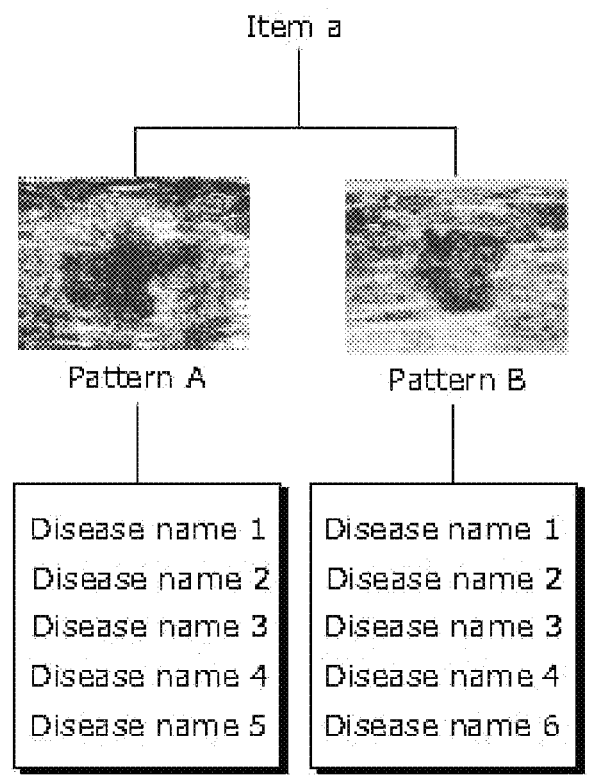
FIG. 4 shows diagnosis flows for explaining degrees of diagnostic difficulty.

In order to evaluate the similarity between the states that are possible as the state of a diagnosis item, it is good to check the total number of disease names commonly derived from both the states that are possible as the state of the diagnosis item. For example, a lot of disease names are commonly included in Pattern A and Pattern B branching from the diagnosis item a as shown in FIG. 4, the states that are Pattern A and Pattern B are not factors that differentiate the disease names. Here, the states do not have features that clearly determine a target disease name. In other words, since the states as the bases for the determination are similar to each other, it is difficult to make the determination based on the states. For this reason, the degree of difficulty of a given diagnosis item in a diagnosis tree is evaluated by counting the total number of disease names derived from the diagnosis item.

Evaluation Indicator Regarding Item (2)

Figure 5:
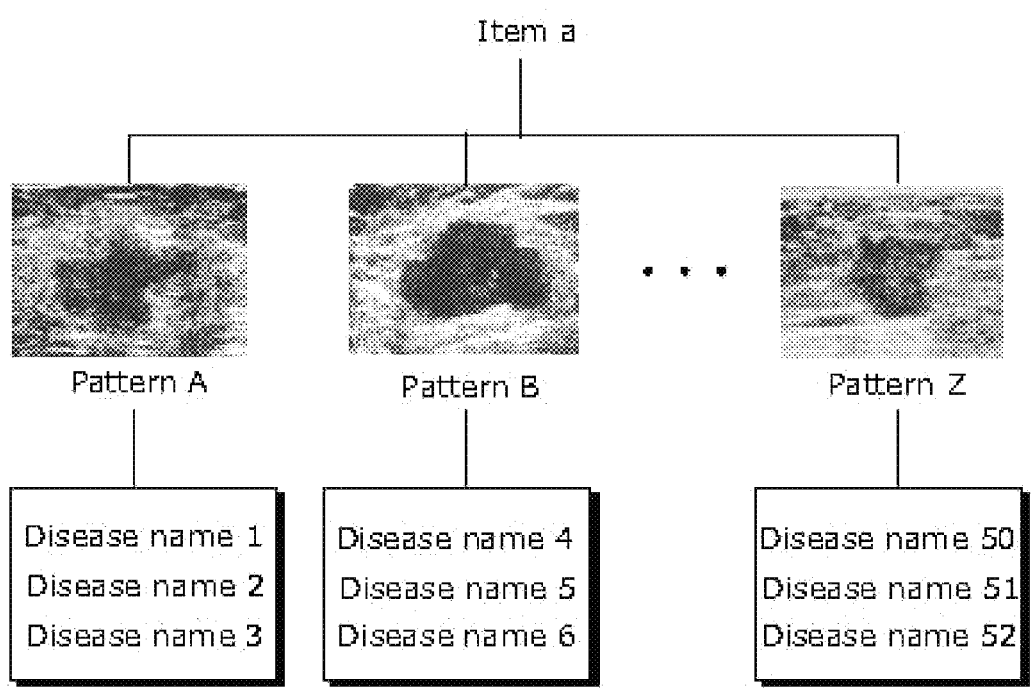
FIG. 5 shows diagnosis flows for explaining degrees of diagnostic difficulty.

In order to evaluate that the total number of the states of a diagnosis item is large with reference to a diagnosis tree, it is good to use the total number of branches below the diagnosis item. In the case of a diagnosis item "Shape" in FIG. 3, the degree of difficulty is evaluated based on the total number of the states (four: Irregular, Polygonal, Lobular, Circular or Elliptical). When the total number of states becomes larger as shown in FIG. 5, the diagnosis item is evaluated as a diagnosis item having a higher degree of difficulty.

Evaluation Indicator Regarding Item (3)

Figure 6:
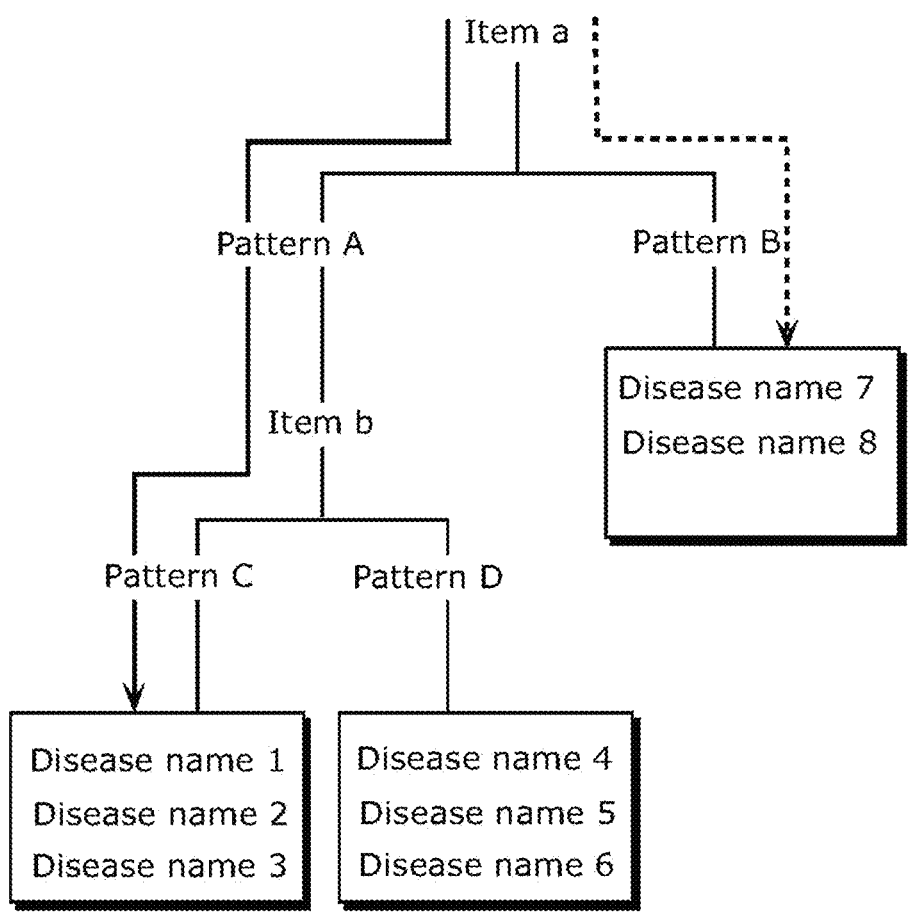
FIG. 6 shows diagnosis flows for explaining degrees of diagnostic difficulty.

In order to evaluate that diagnosing diagnosis items with reference to a diagnosis tree do not determine a disease name, it is good to use the total number of diagnosis items included in the diagnosis tree. When the flow shown by a solid-line arrow and the flow shown by a dotted-line arrow are compared with each other in a diagnosis tree shown in FIG. 6, the solid-line arrow shows the flow that includes the larger number of diagnoses, and thus is more difficult than the other.

Evaluation Indicator Regarding Item (4)

Figure 7:
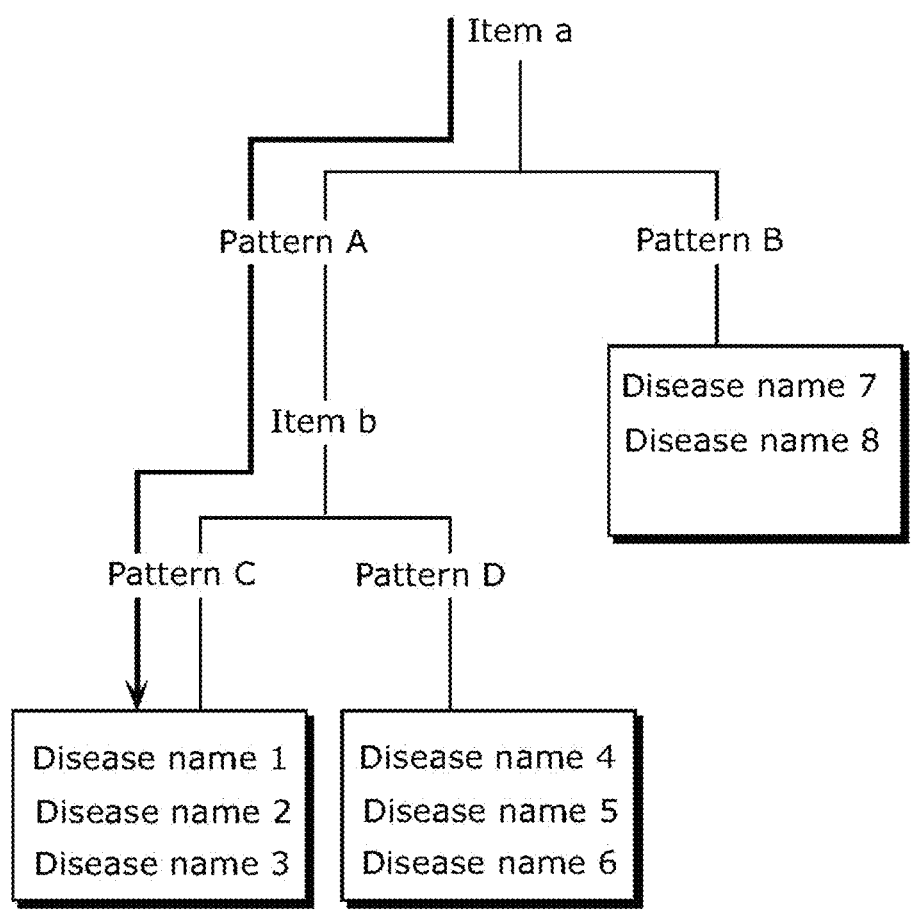
FIG. 7 shows diagnosis flows for explaining degrees of diagnostic difficulty.

A description is given of a case where diagnosing all diagnosis items does not determine a disease name. It is assumed here that diagnosis items are diagnosed as shown by the arrow in a diagnosis tree shown in FIG. 7. In this case, one of Disease names 1, 2, and 3 must be determined even after the diagnoses of all the diagnosis items are completed. At this time, it is good to evaluate the degree of difficulty based on the total number of disease names in the diagnosis tree. For example, the total number of Disease names 1, 2, and 3 are three in FIG. 7. In FIG. 3, the degree of difficulty is evaluated based on the total number of disease names (two) derived with reference to the diagnosis tree including the diagnosis that the border part is clear and smooth and the diagnosis that the shape of the border part is irregular.

There may be a case where it is difficult to narrow down to a disease name even when the total number of disease names is small. In such a case, the likelihood of misdiagnosing each disease name as another disease is evaluated. Here, the likelihood of misdiagnosis is calculated based on an indicator indicating how many times the image interpretation results indicated by image interpretation reports are changed in later diagnoses. A final diagnosis is made through two stages roughly divided into: the first stage in which radiologists interpret images; and the second stage in which a clinician makes the definitive diagnosis with reference to the image interpretation results. At this time, it is possible to determine, as the likelihood of misdiagnosis, the probability that the disease name finally determined by the clinician is different from the disease name determined at the time of the image interpretations. The stage of image interpretations by radiologists is composed of a first image interpretation and a second image interpretation. Thus, it is possible to determine, as the likelihood of misdiagnosis, the probability that the results of the first and second image interpretations are different. Hereinafter, these results are collectively described as disease data.

Evaluation Indicator Regarding Item (5)

Figure 8:
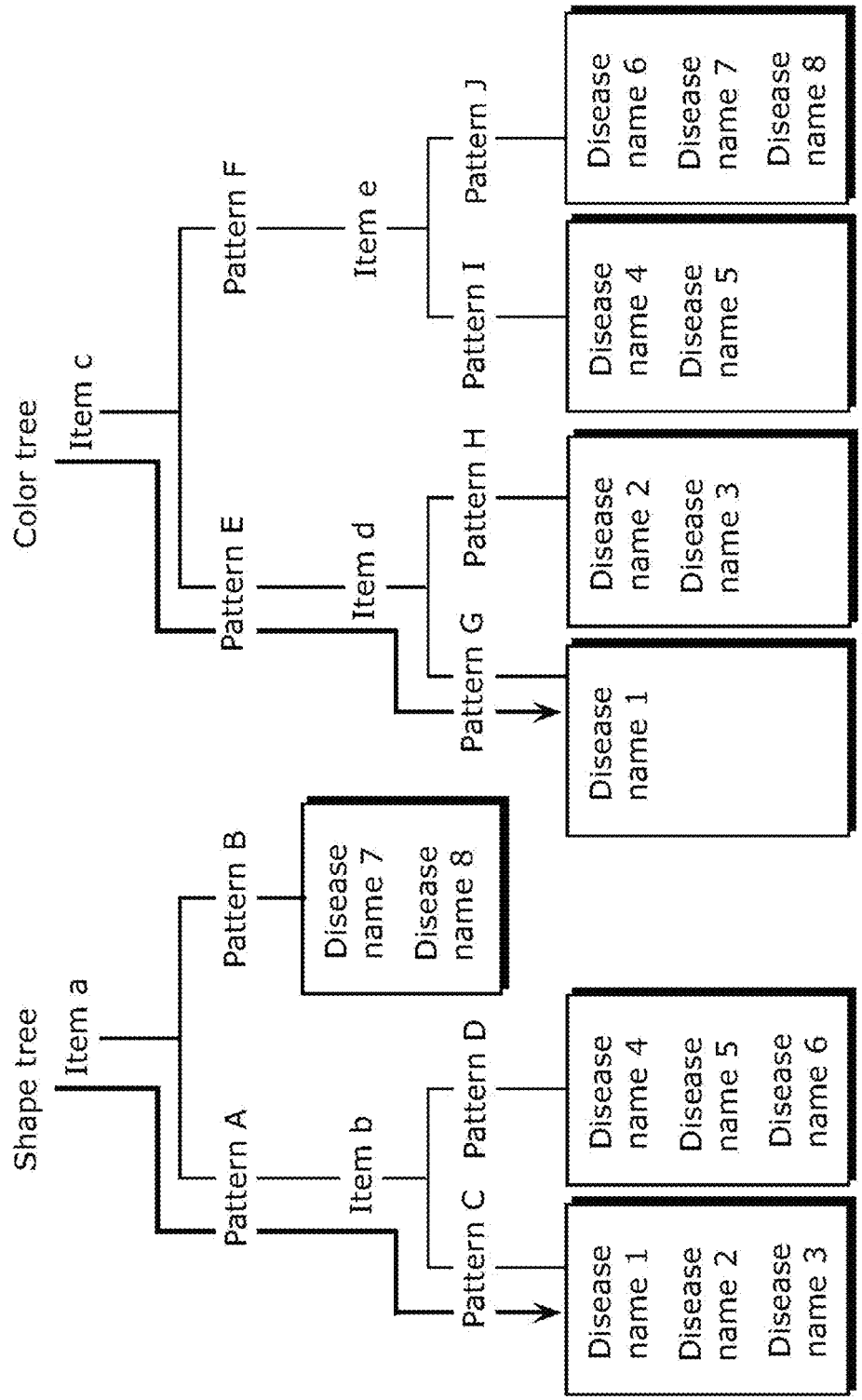
FIG. 8 shows diagnosis trees for explaining degrees of diagnostic difficulty.

In order to evaluate that only a single-kind diagnosis item does not determine a disease name, it is good to calculate the total number of diagnosis trees used by extracting the total number of items from image interpretation reports. A description is given of a case of using a diagnosis tree of shapes (shape tree) and a diagnosis tree of colors (color tree) as shown in FIG. 8. It is assumed here that Disease name is finally determined by making diagnoses according to the respective arrows. In this case, the image interpretation reports include a character string (such as "Item a") related to each of the diagnosis trees. Accordingly, it is possible to find out how many diagnosis trees are used by analyzing the character string in the image interpretation report and applying the character string to each diagnosis tree. Here, a larger number of diagnosis trees indicates a more complicated diagnosis and leads to the evaluation that the degree of diagnostic difficulty is higher.

The embodiment described later shows an exemplary method which makes it possible to effectively change cases to be presented by using diagnosis trees in combination, instead of showing an approach for evaluating the degrees of difficulty based on the total number of diagnoses trees used.

In this way, based on the evaluation indicators, it is possible to estimate the degrees of difficulty in diagnosing the diagnosis items from the diagnosis trees. Calculation of the degrees of difficulty is described specifically in the embodiment.

In view of the above, the Inventors of the present application have arrived at enabling searches of desired similar cases by estimating the degrees of difficulty from image interpretation reports and diagnosis trees each including diagnosis flows.

As a result, a similar case search apparatus according to an aspect of the present invention has been made which includes: a keyword extracting unit configured to extract a keyword from an image interpretation report that is document data including a diagnosis item and a diagnosis result, the diagnosis item being a diagnosis target in interpretation of a medical image, and the diagnosis result showing a state of the diagnosis item; a diagnosis tree analyzing unit configured to extract, based on the keyword, one or more target diagnosis flows corresponding to the image interpretation report, by referring to a diagnosis tree storage unit storing one or more diagnosis trees each of which includes a plurality of diagnosis flows each including a diagnosis item and a state of the diagnosis item which are used to determine a disease name; a similar diagnosis flow extracting unit configured to extract one or more similar diagnosis flows similar to the one or more target diagnosis flows from among the plurality of diagnosis flows included in the diagnosis trees stored in the diagnosis tree storage unit, based on a degree of difficulty regarding a diagnosis item or a degree of difficulty regarding a disease name, the degree of difficulty regarding a diagnosis item being a degree of difficulty in determining a state of a diagnosis item, and the degree of difficulty regarding a disease name being a degree of difficulty in determining a disease name; and a similar case search unit configured to search out one or more case data sets corresponding to the one or more similar diagnosis flows from among a plurality of case data sets stored in a case data storage unit.

With this structure, it is possible to search out the case data set using the similar diagnosis flow extracted based on the degrees of difficulty. Accordingly, it is possible to effectively search for the case data set focusing on the diagnosis items or disease names having the high degrees of difficulty, and to thereby search out the appropriate case data set.

For example, the degree of difficulty regarding a disease name may increase with an increase in a total number of diagnosis flows commonly including a matching disease name in the diagnosis trees. For example, the degree of difficulty regarding a diagnosis item may increase with an increase in a total number of states branching from a diagnosis item in the diagnosis trees. For example, the degree of difficulty regarding a disease name may increase with an increase in a total number of disease names derived from states branching from a diagnosis item in one of the diagnosis trees. For example, the degree of difficulty regarding a disease name may increase with an increase in a value that is preset for a disease name and indicating a likelihood of misdiagnosis.

According to at least one of these structures, it is possible to increase the degree of difficulty of the diagnosis item or the disease name that often confuses a doctor in making a diagnosis, and to thereby search out the appropriate case data set.

For example, the similar diagnosis flow extracting unit may e configured to extract the one or more similar diagnosis flows for each diagnosis tree, when a total number of the one or more target diagnosis flows extracted is at least two and the at least two target diagnosis flows are included in different diagnosis trees.

For example, the similar diagnosis flow extracting unit may be configured to extract the one or more similar diagnosis flows from among the plurality of diagnosis flows in the diagnosis trees stored in the diagnosis tree storage unit such that one or more similar diagnosis flows each having a higher degree of difficulty regarding a diagnosis item or a higher degree of difficulty regarding a disease name are more likely to be extracted as the one or more similar diagnosis flows.

With this structure, it is possible to extract the similar diagnosis flows even when the plurality of target diagnosis flows is extracted.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

An embodiment is described below with reference to the drawings. The embodiment below shows a generic example. The numerical values, shapes, materials, structural elements, the arrangement and connection of the structural elements, steps, the processing order of the steps etc. shown in the following exemplary embodiment are mere examples, and therefore do not limit the scope of the appended claims and their equivalents. Therefore, among the structural elements in the following exemplary embodiment, structural elements not recited in any one of the independent claims are described as arbitrary structural elements.

(Embodiment)

Figure 9:
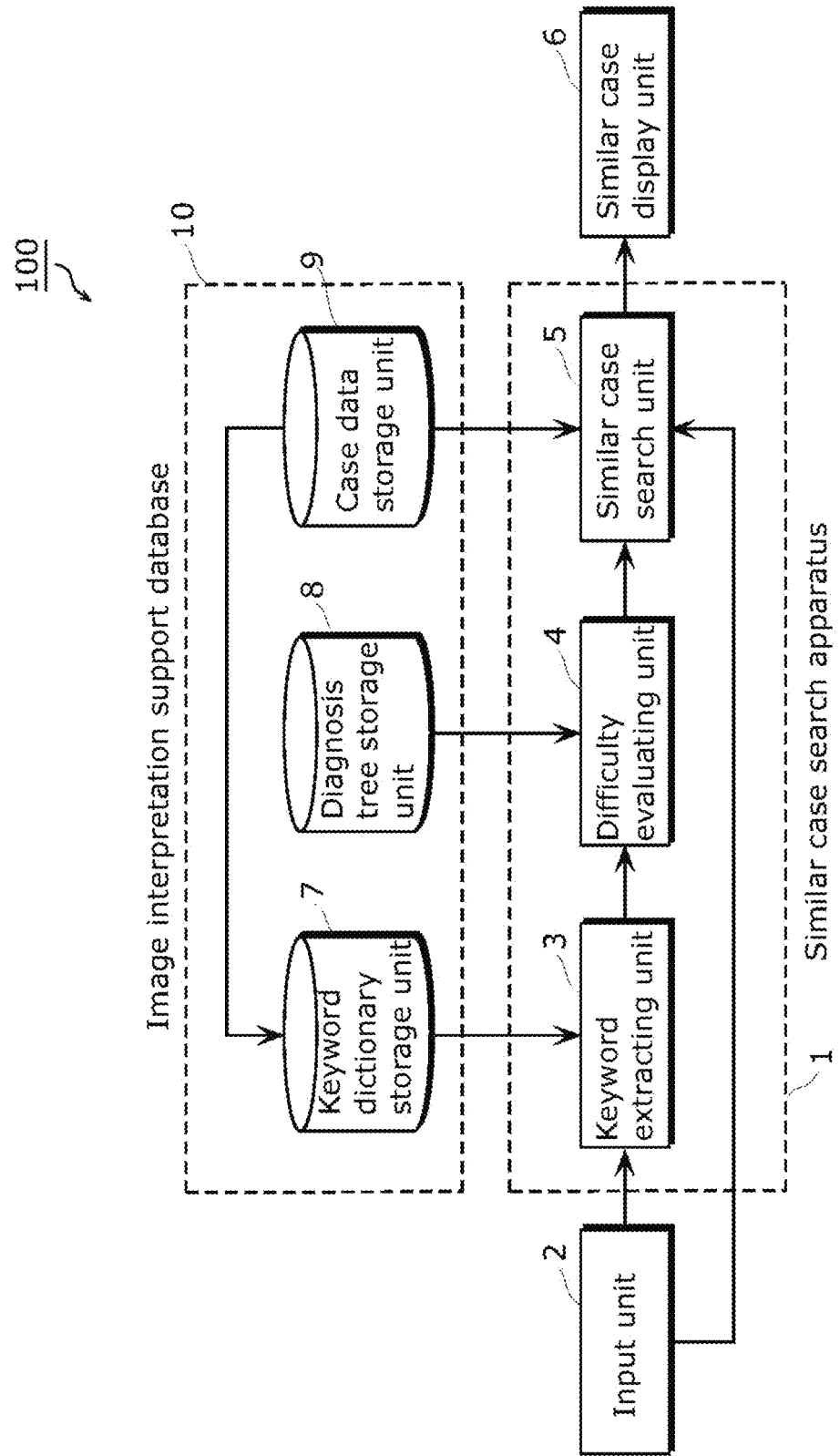
FIG. 9 is a block diagram of a functional structure of a similar case search system according to an embodiment.

FIG. 9 is a block diagram of a functional structure of a similar case search system 100 according to this embodiment. As shown in FIG. 9, the similar case search system 100 includes a similar case search apparatus 1, an input unit 2, a similar case display unit 6, and an image interpretation support database 10.

(Input Unit 2)

The input unit 2 is a device (such as a keyboard or a mouse) used by a doctor to input an image interpretation report. The input unit 2 forwards the text data input by a doctor or the selection result to a keyword extracting unit 3.

(Similar Case Display Unit 6)

The similar case display unit 6 receives case data from the similar case search unit 5, and presents the case data to the doctor. The similar case display unit 6 is, for example, a display for a personal computer (PC), a television set (TV), or a medical image interpretation monitor.

(Similar Case Search Apparatus 1)

The similar case search apparatus 1 is an apparatus for searching a case data storage unit 9 for case data similar to the image interpretation report input by the input unit 2. The similar case search apparatus 1 includes a keyword extracting unit 3, a difficulty evaluating unit 4, and a similar case search unit 5.

(Keyword Extracting Unit 3)

The keyword extracting unit 3 receives text data of the image interpretation report from the input unit 2, extracts keywords related to the medial terms, diagnosis items, and diagnosis results from the text data, and forwards these keywords to the difficulty evaluating unit 4. In short, the keyword extracting unit 3 receives the image interpretation report from the input unit 2, and extracts the keywords from the received image interpretation report.

Figure 10:
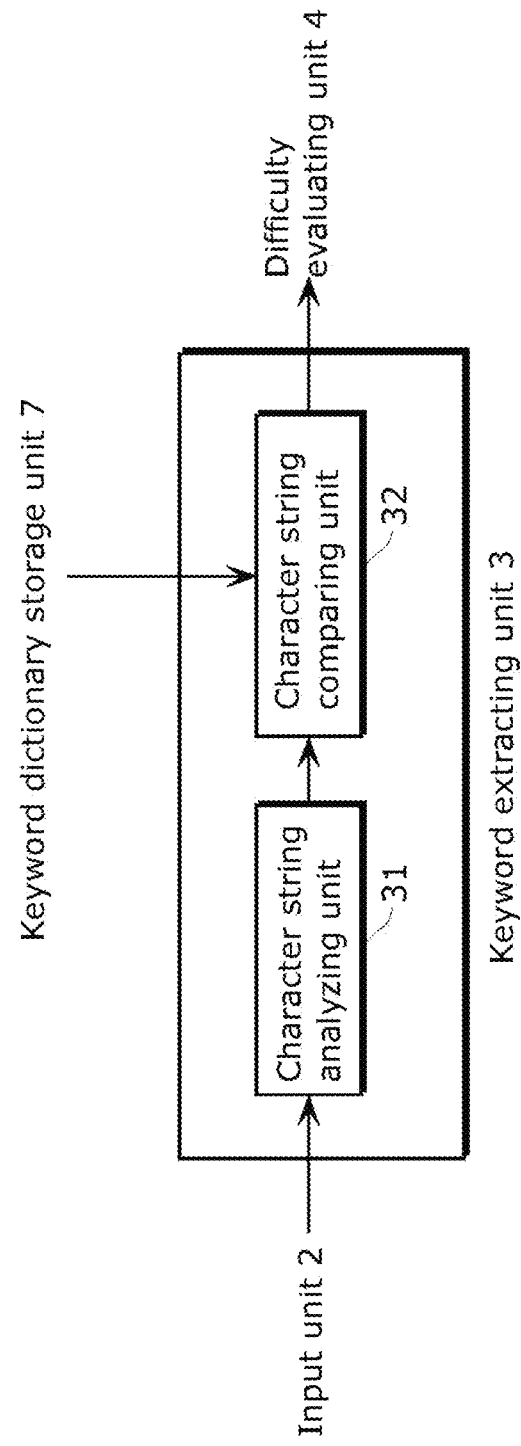
FIG. 10 is a block diagram of a detailed functional structure of a keyword extracting unit.

FIG. 10 is a block diagram of a detailed functional structure of the keyword extracting unit 3. As shown in FIG. 10, the keyword extracting unit 3 includes a character string analyzing unit 31 and a character string comparing unit 32.

The character string analyzing unit 31 analyzes character strings in the image interpretation report received from the input unit 2, and classifies the character strings into nouns, postpositional particles (of Japanese), etc. Next, the character string analyzing unit 31 forwards the analyzed character strings to the character string comparing unit 32.

The character string comparing unit 32 receives the character strings analyzed by the character string analyzing unit 31, compares each of the character strings and character strings stored as keywords in a keyword dictionary storage unit 7, and, when there are matching keywords (character strings), forwards the matching keywords to the difficulty evaluating unit 4.

(Difficulty Evaluating Unit 4)

The difficulty evaluating unit 4 receives the character strings extracted by the keyword extracting unit 3, and reads out the diagnosis tree including the matching character strings from a diagnosis tree storage unit 8. The difficulty evaluating unit 4 calculates the degree of difficulty regarding the diagnosis item from these character strings and the diagnosis tree, and forwards the degree of difficulty to the similar case search unit 5.

Figure 11:
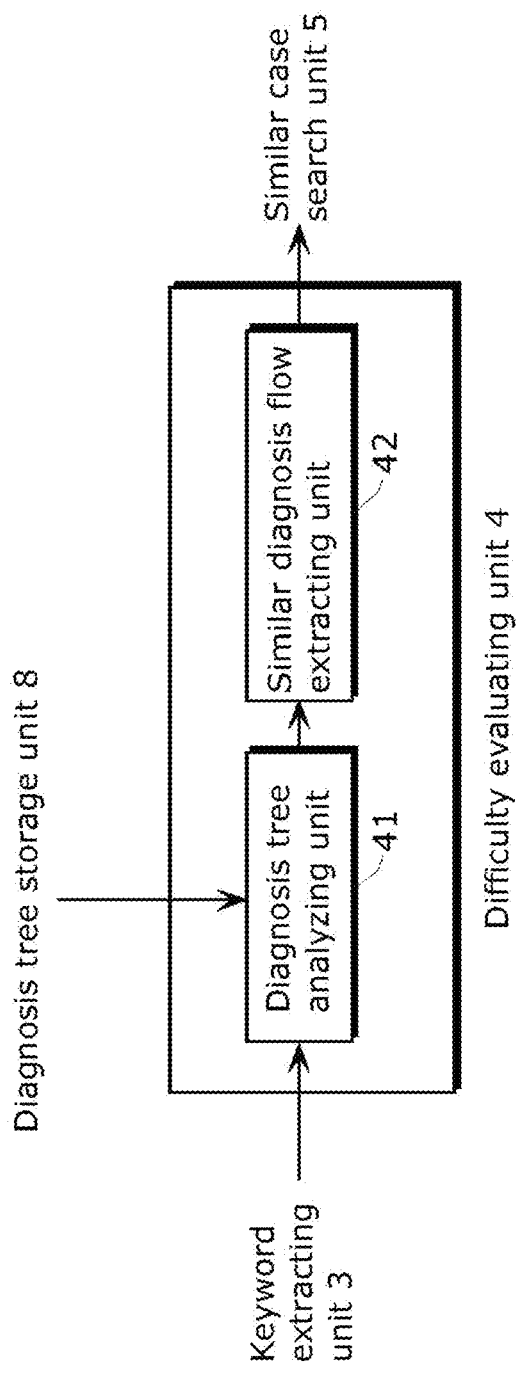
FIG. 11 is a block diagram of a detailed functional structure of a difficulty evaluating unit.

FIG. 11 is a block diagram of a detailed functional structure of the difficulty evaluating unit 4. As shown in FIG. 11, the difficulty evaluating unit 4 includes a diagnosis tree analyzing unit 41 and a similar diagnosis flow extracting unit 42.

With reference to the diagnosis tree storage unit 8, the diagnosis tree analyzing unit 41 extracts a target diagnosis flow that is a diagnosis flow corresponding to the image interpretation report input by the input unit 2, based on the keywords extracted by the keyword extracting unit 3.

More specifically, the diagnosis tree analyzing unit 41 compares each of the character strings received from the keyword extracting unit 3 with character strings in the diagnosis trees stored in the diagnosis tree storage unit 8, and selects the diagnosis trees including the keywords. Next, the diagnosis tree analyzing unit 41 analyzes which one of the diagnosis flows in the diagnosis tree corresponds to the current image interpretation report, based on the selected diagnosis trees and character strings. Next, the diagnosis tree analyzing unit 41 forwards, to the similar diagnosis flow extracting unit 42, the diagnosis trees and intra-tree position information (target diagnosis flows) corresponding to the current image interpretation report.

Based on the degree of difficulty regarding the diagnosis item or the degree of difficulty regarding the disease name, the similar diagnosis flow extracting unit 42 extracts a similar diagnosis flow similar to the target diagnosis flow from among the plurality of diagnosis flows included in the diagnosis trees stored in the diagnosis tree storage unit 8. More specifically, the similar diagnosis flow extracting unit 42 extracts the one or more similar diagnosis flows from among the plurality of diagnosis flows such that one or more similar diagnosis flows each having a higher degree of difficulty regarding a diagnosis item or a higher degree of difficulty regarding a disease name are more likely to be extracted as the one or more similar diagnosis flows.

More specifically, the similar diagnosis flow extracting unit 42 receives the diagnosis tree and the intra-tree position information, and obtains the degree of difficulty regarding the diagnosis item included in the target diagnosis flow corresponding to the current image interpretation report. Next, the similar diagnosis flow extracting unit 42 extracts the diagnosis flow including the higher degree of difficulty regarding the diagnosis item as the similar diagnosis flow, and forwards the similar diagnosis flow to the similar case search unit 5.

(Similar Case Search Unit 5)

The similar case search unit 5 receives the similar diagnosis flow from the difficulty evaluating unit 4, calculates the degrees of similarity of the case data sets in the case data storage unit 9, and forwards one of the case data sets having a high degree of similarity to the similar case display unit 6. In other words, the similar case search unit 5 searches out the case data set corresponding to the similar diagnosis flow from among the plurality of case data sets stored in the case data storage unit 9. In short, the similar case search unit 5 searches out the case data set obtained in a diagnosis made according to the similar diagnosis flow. Furthermore, the similar case search unit 5 searches out the case data set obtained in a diagnosis made according to the target diagnosis flow.

Figure 12:
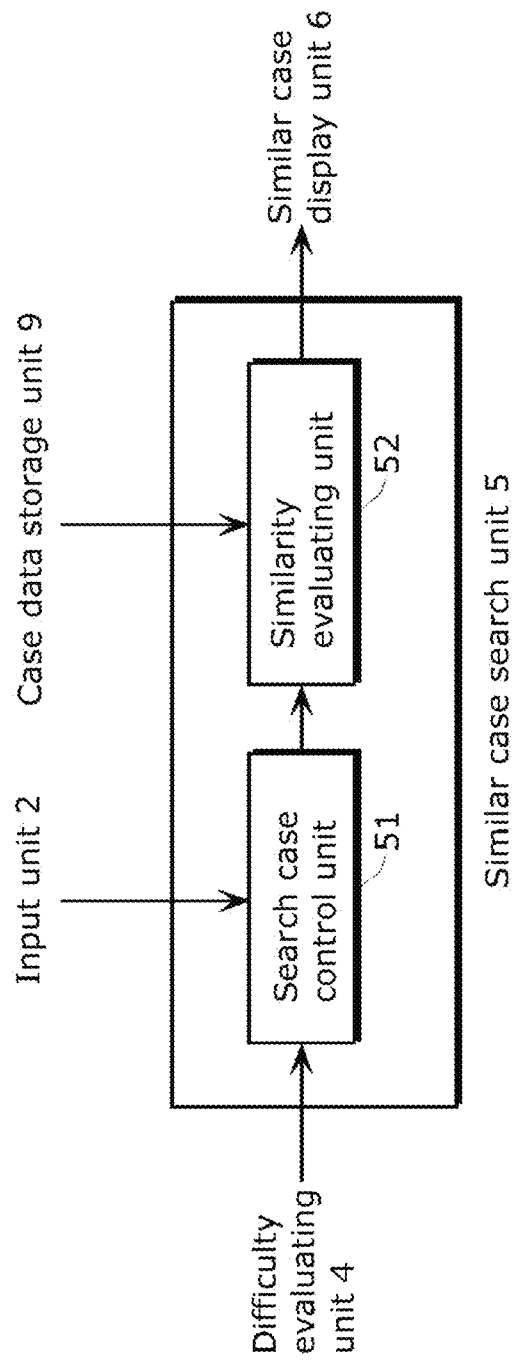
FIG. 12 is a block diagram of a detailed functional structure of a similar case search unit.

FIG. 12 is a block diagram of a detailed functional structure of the similar case search unit 5. As shown in FIG. 12, the similar case search unit 5 includes a search case control unit 51 and a similarity evaluating unit 52.

The search case control unit 51 receives the similar diagnosis flow from the difficulty evaluating unit 4. Here, if there is no input from the input unit 2, the search case control unit 51 forwards the raw similar diagnosis flow to the similarity evaluating unit 52. On the other hand, when there is an input from the input unit 2, the search case control unit 51 adds a weight to the similar diagnosis flow, and forwards the similar diagnosis flow with the weight to the similarity evaluating unit 52.

The similarity evaluating unit 52 receives the similar diagnosis flow, and calculates the degree of similarity between the diagnosis flow of the case data set stored in the case data storage unit 9 and the similar diagnosis flow. Next, the similarity evaluating unit 52 forwards the case data set having the high degree of similarity to the similar case display unit 6.

(Image Interpretation Support Database 10)

The image interpretation support database 10 includes the keyword dictionary storage unit 7, the diagnosis tree storage unit 8, and the case data storage unit 9.

(Keyword Dictionary Storage Unit 7)

The keyword dictionary storage unit 7 stores medical terms for use in keyword extraction.

(Diagnosis Tree Storage Unit 8)

The diagnosis tree storage unit 8 stores information such as diagnosis items and the states of the diagnosis items related to diagnosis flows. In other words, the diagnosis tree storage unit 8 stores diagnosis trees each represented in the form of a tree and including a plurality of diagnosis flows each including diagnosis items considered in order to finally determine a disease name and the states of the diagnosis items.

(Case Data Storage Unit 9)

The case data storage unit 9 stores past image interpretation reports and medical images used to make diagnoses. In short, the case data storage unit 9 stores case data sets each of which is a set of an image interpretation report and medical images.

(Utility Form of Similar Case Search System)

Figure 13:
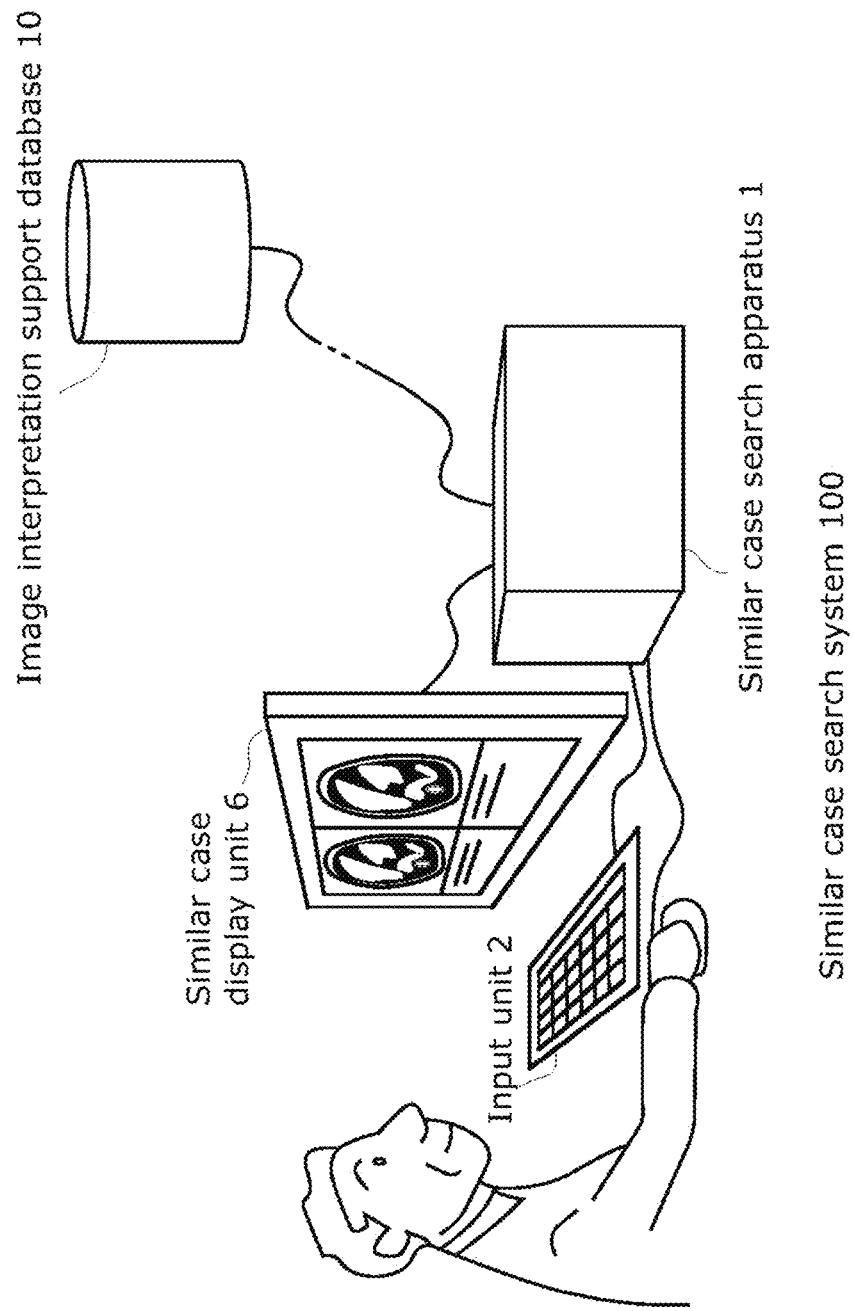
FIG. 13 is an illustration showing a utility form of the similar case search system according to the embodiment.

FIG. 13 is a block diagram of a utility form of the similar case search system 100 according to this embodiment.

The similar case search system 100 includes the similar case search apparatus 1, the input unit 2, the similar case display unit 6, and the image interpretation support database 10. The similar case search system 100 enables the degrees-of-difficulty evaluation based on the image interpretation report input by the input unit 2, searches the image interpretation support database 10 for case data sets each having high degrees of difficulty with respect to the input image interpretation report, and presents the search results to the similar case display unit 6.

Next, a description is given of various kinds of operations performed by the similar case search system 100 configured as described above.

(Outline of the Entire Processes in Similar Case Search)

Figure 14:
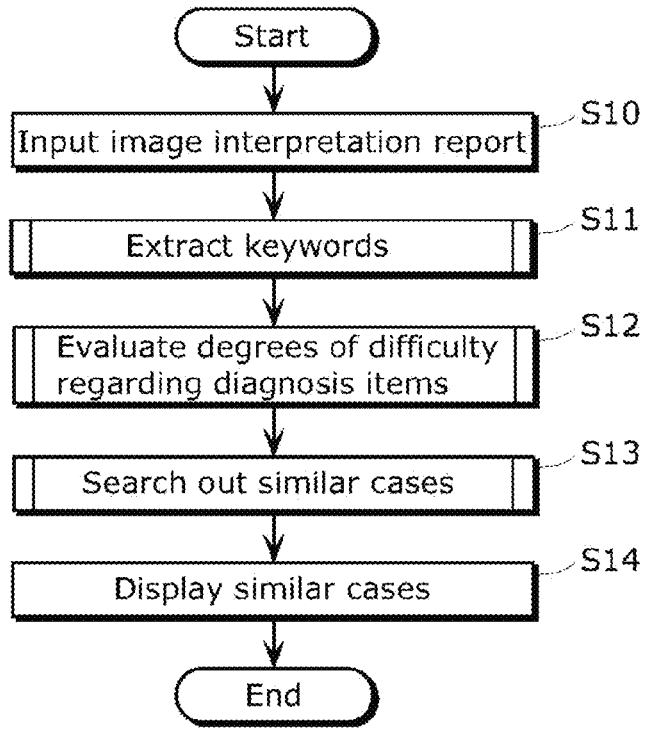
FIG. 14 is a flowchart of processes performed in the similar case search system according to the embodiment.

FIG. 14 is a flowchart of processes performed by the similar case search system 100. FIG. 14 corresponds to Steps S03 and S07 in FIG. 1.

(Flow of Processes Performed by Similar Case Search System)

(S10: Input of Image Interpretation Report)

In Step S10, the input unit 2 receives the image interpretation report from the doctor, and forwards the image interpretation report to the similar case search apparatus 1. Here, a specific description is given taking an exemplary case where the doctor inputs the comments that "The border part is clear and smooth, and the shape of the border part is irregular. Thus, the papillotubular carcinoma is suspected. In Step S10, the doctor's input that "The border part is clear and smooth, and the shape of the border part is irregular. Thus, the papillotubular carcinoma is suspected." is forwarded to the similar case search apparatus 1.

(S11: Keyword Extraction)

Figure 15:
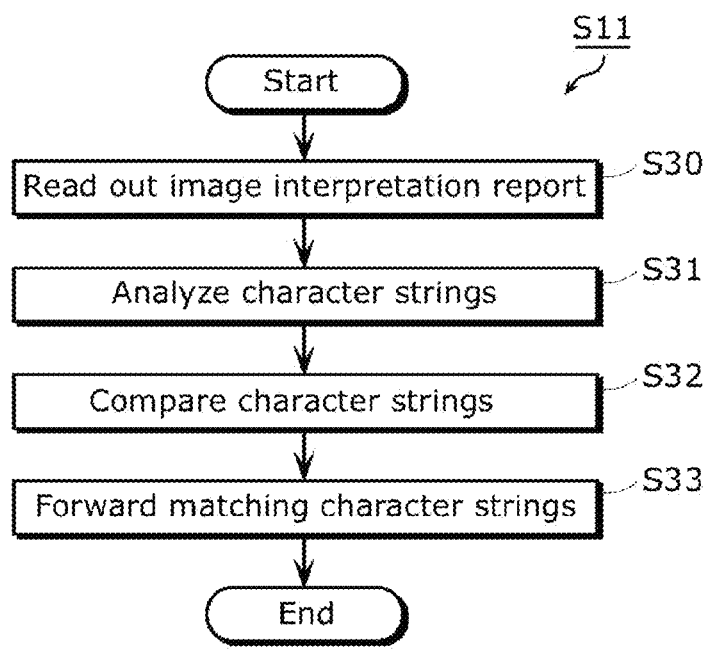
FIG. 15 is a flowchart of processes performed by the keyword extracting unit.

In Step S11, the keyword extracting unit 3 receives text data of the image interpretation report, extracts character strings related to a current diagnosis from the text data, and forwards the character strings to the difficulty evaluating unit 4. Hereinafter, the details of Step S11 are described with reference to FIG. 15.

In Step S30, the keyword extracting unit 3 reads out the image interpretation report received from the input unit 2.

In Step S31, the character string analyzing unit 31 analyzes character strings in the image interpretation report received from the input unit 2, and classifies the character strings into nouns, postpositional particles (of Japanese), etc. Next, the character string analyzing unit 31 forwards the analyzed character strings to the character string comparing unit 32.

In Step S32, the character string comparing unit 32 receives the analyzed character strings from the character string analyzing unit 31, and compares the analyzed character strings with the character strings stored in the keyword dictionary storage unit 7.

In Step S33, the character string comparing unit 32 forwards, to the difficulty evaluating unit 4, only the matching character strings that match the character strings received from the character string analyzing unit 31 from among the character strings stored in the keyword dictionary storage unit 7. In the exemplary case where an input that "The border part is clear and smooth, and the shape of the border part is irregular. Thus, the papillotubular carcinoma is suspected." is received in Step S10, the character string analyzing unit 31 analyzes the character stings included in "The border part is clear and smooth, and the shape of the border part is irregular" in Step S11. For example, the character string comparing unit 32 divides the sentences into character strings such that "The border part /is/ clear and smooth, /and/ the shape /of/ the border part /is/ irregular. Thus, /the papillotubular carcinoma/ is suspected.". Here, these slashes show where the words are divided in the sentences. Next, the character string analyzing unit 31 compares each of the character stings obtained by the division with the character strings (such as border part, clear and smooth, shape, irregular, and papillotubular carcinoma) stored in the keyword dictionary storage unit 7, and forwards the character strings "border part", "clear and smooth", "shape", "irregular", and "papillotubular carcinoma" to the difficulty evaluating unit 4.

(S12: Evaluation of the Degrees of Difficulty Regarding Diagnosis Items)

Figure 16:
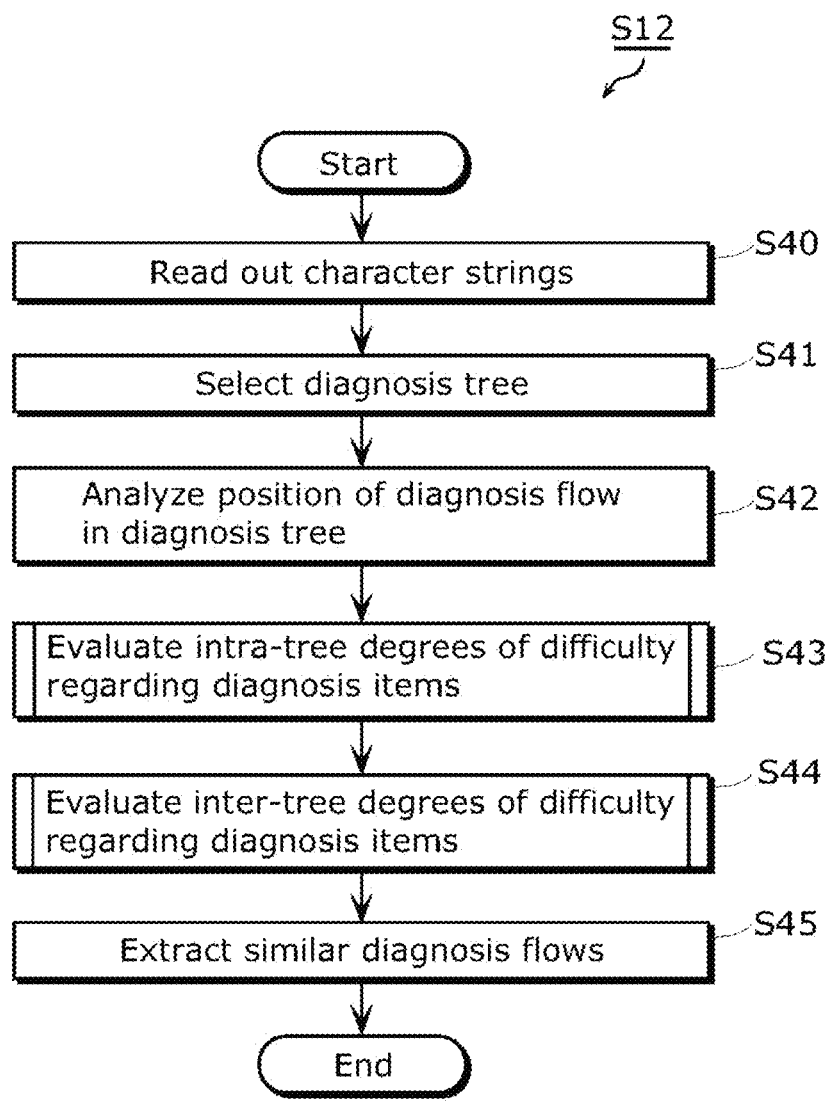
FIG. 16 is a flowchart of processes performed by the difficulty evaluating unit.

In Step S12, the difficulty evaluating unit 4 receives the character strings extracted by the keyword extracting unit 3, and reads out the diagnosis tree including the matching character strings from the diagnosis tree storage unit 8. The difficulty evaluating unit 4 calculates the degree of difficulty of the diagnosis item from these character strings and the diagnosis tree, and forwards the degree of difficulty to the similar case search unit 5. Hereinafter, the details of Step S12 are described with reference to FIG. 16.

In Step S40, the difficulty evaluating unit 4 reads out the character strings received from the keyword extracting unit 3.

In Step S41, the diagnosis tree analyzing unit 41 compares the character strings received from the keyword extracting unit 3 with the diagnosis trees stored in the diagnosis tree storage unit 8, and selects the diagnosis tree. In short, with reference to the diagnosis tree storage unit 8, the diagnosis tree analyzing unit 41 determines the diagnosis tree including the diagnosis items, the states of the diagnosis items, and the disease names that match the keywords extracted by the keyword extracting unit 3.

In Step S42, the diagnosis tree analyzing unit 41 analyzes the position of the diagnosis flow corresponding to the current image interpretation report in the selected diagnosis tree, based on the received character strings and the selected diagnosis tree. Next, the diagnosis tree analyzing unit 41 forwards, to the similar diagnosis flow extracting unit 42, the diagnosis tree and information about the position of the diagnosis flow corresponding to the current image interpretation report in the selected diagnosis tree (this information is referred to as intra-tree position information). In short, the diagnosis tree analyzing unit 41 forwards the diagnosis flow corresponding to the current image interpretation report as the target diagnosis flow to the similar diagnosis flow extracting unit 42.

In Step S43, the similar diagnosis flow extracting unit 42 receives the diagnosis tree and the intra-tree position information, and calculates the degree of difficulty regarding each diagnosis item that is also included in the current image interpretation report. An exemplary case is considered here in which, in Step S11, the following character strings are extracted as keywords: "border part", "clear and smooth", "shape", "irregular", and "papillotubular carcinoma". At this time, the diagnosis tree analyzing unit 41 compares each of the keywords "border part", "clear and smooth", "shape", "irregular", and "papillotubular carcinoma" and each of the character strings in the diagnosis tree in FIG. 3, and extracts the target diagnosis flow corresponding to the current image interpretation report. Hereinafter, evaluation of the degrees of difficulty is explained using the target diagnosis flow extracted in this way.

(S43: Evaluation of the Degrees of Difficulty in Diagnosis Tree)

In Step S43, the similar diagnosis flow extracting unit 42 calculates the degrees of difficulty that is used to extract a similar diagnosis flow.

(First Difficulty Pattern: Calculating the Degree of Difficulty Based on the Total Number of Disease Names Commonly Derived According to a Plurality of Diagnosis Flows)

Figure 17:
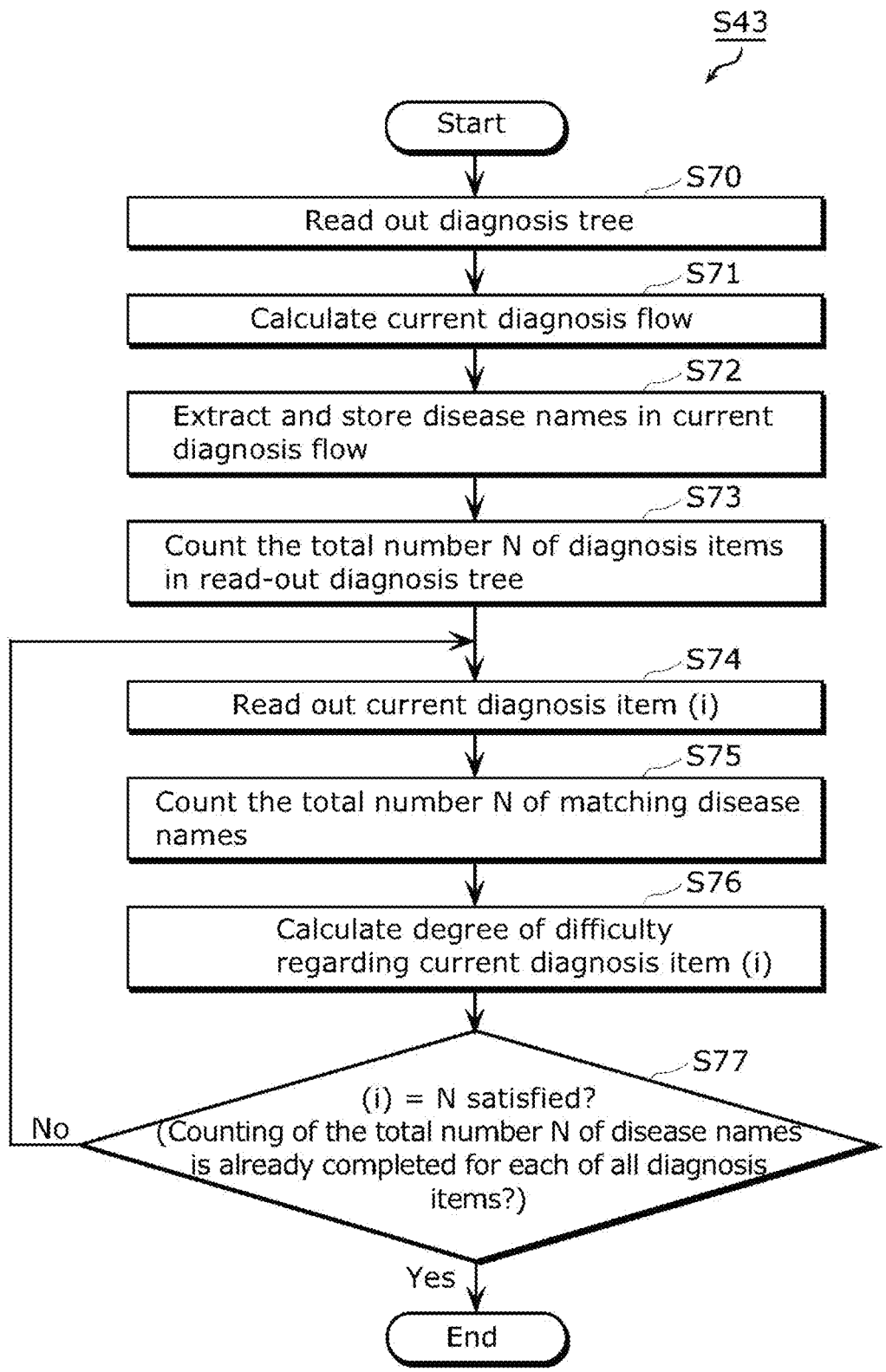
FIG. 17 is a flowchart of processes performed by a similar diagnosis flow extracting unit.

It is to be noted that, in Step S43, the degree of difficulty may be determined based on the total number of disease names commonly derived from some of diagnosis flows branching from a diagnosis item (hereinafter also referred to as the total number of matching disease names). It is difficult to make a definitive diagnosis when diagnosing all diagnosis items does not determine the disease name. For this reason, the similar diagnosis flow extracting unit 42 evaluates the degree of difficulty based on how many matching disease names are derived below the branches of the diagnosis item. More specifically, the similar diagnosis flow extracting unit 42 evaluates that the degree of difficulty regarding a disease name is higher as the disease name is derived according to a lager number of diagnosis flows, and that the degree of difficulty regarding a disease name is lower as the disease name is derived according to a smaller number of diagnosis flows. In short, the similar diagnosis flow extracting unit 42 calculates the degree of difficulty regarding the disease name such that the degree of difficulty regarding the disease name becomes higher as a larger number of diagnosis flows yields the same disease name. Hereinafter, the details of Step S43 are described with reference to FIG. 17.

In Step S70, the similar diagnosis flow extracting unit 42 reads out the diagnosis tree.

In Step S71, the similar diagnosis flow extracting unit 42 calculates the current diagnosis flow.

In Step S72, the similar diagnosis flow extracting unit 42 extracts and stores the disease names in the current diagnosis flow (hereinafter also referred to as the current flow).

In Step S73, the similar diagnosis flow extracting unit 42 counts the total number N of diagnosis items in the read-out diagnosis tree.

In Step S74, the similar diagnosis flow extracting unit 42 reads out a current diagnosis item (i).

In Step S75, the similar diagnosis flow extracting unit 42 counts the total number N of matching disease names stored in Step S72 from among the disease names included in the flow including the current diagnosis item (i).

In Step S76, the similar diagnosis flow extracting unit 42 calculates the degree of difficulty regarding the diagnosis item based on the total number of disease names commonly derived according to the plurality of diagnosis flows.

In Step S77, a check is made as to whether or not (i)=N is satisfied, more specifically, whether or not counting of the total number of disease names is already completed for each of all the diagnosis items. A transition to End is made when the counting for all the diagnosis items is already completed. Otherwise, a transition to Step S74 is made to continue counting the total number N of matching disease names.

A description is given of a specific exemplary case of calculating the degree of difficulty based on the total number of matching disease names commonly derived from a plurality of diagnosis flows with reference to FIG. 3. See the part below the diagnosis item "Shape" to focus on the kinds of possible states "Irregular", "Polygonal", and "Lobular". As disease names below "Irregular", "Papillotubular carcinoma" and "Solidtubular carcinoma" are found. As disease names below "Polygonal", "Solidtubular carcinoma", "Mucinous carcinoma", and "Medullary carcinoma" are found. As disease names below "Lobular", "Lobular tumor", "Fibroadenoma", and "Cyst" are found. At this time, the degree of difficulty of "Irregular" is evaluated as high because the disease name "Solidtubular carcinoma" included below "Irregular" is also found below "Polygonal", and therefore it is difficult to differentiate these states. On the other hand, "Lobular" is easy to differentiate because the disease name "Solidtubular carcinoma" is not found, and is evaluated as having a low degree of difficulty.

(Second Difficulty Pattern: Calculating the Degree of Difficulty Based on the Total Number of Branches from Each Diagnosis Item)

Figure 18:
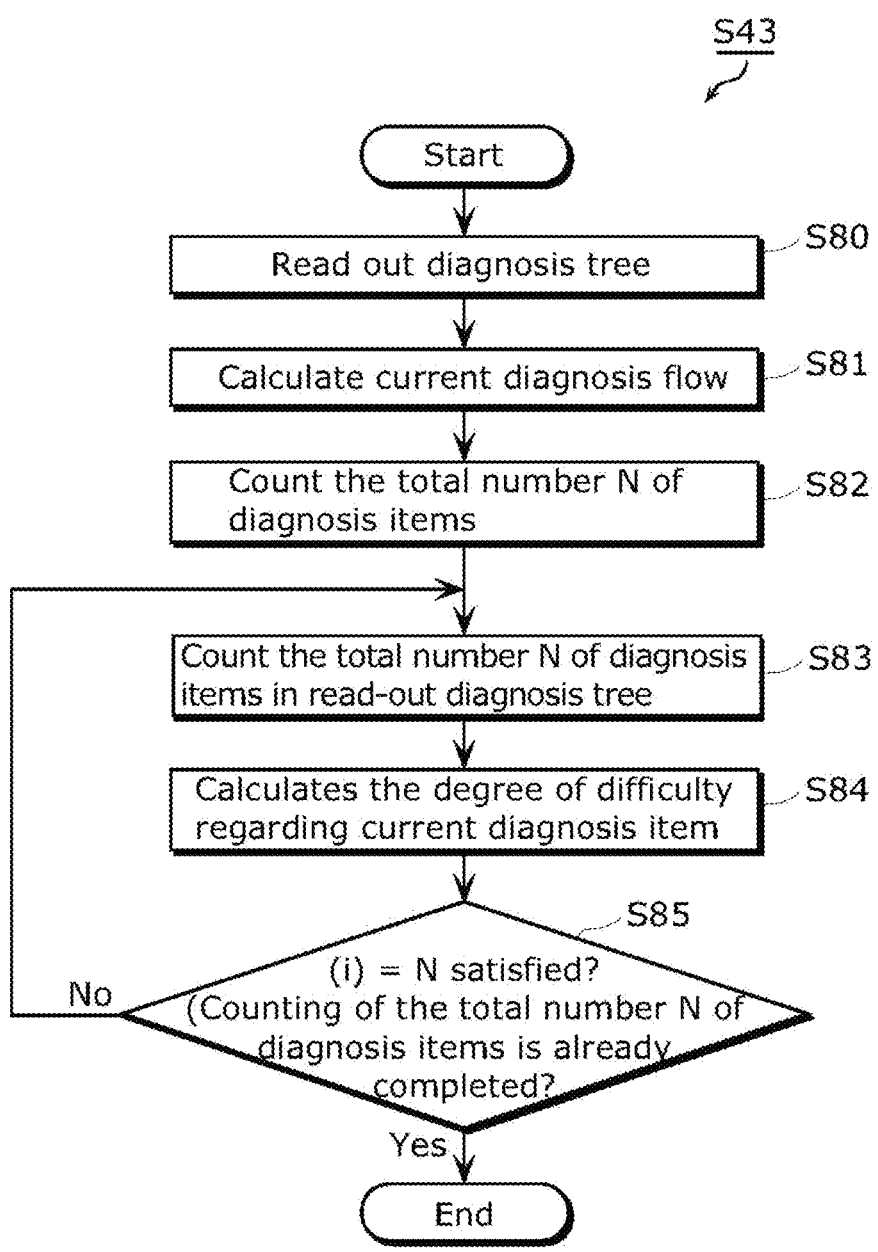
FIG. 18 is a flowchart of processes performed by the similar diagnosis flow extracting unit.

It is to be noted that, in Step S43, the degree of difficulty may be determined based on the total number of branches from the diagnosis item. A larger number of states of a diagnosis item makes it more difficult to diagnose. For this reason, the degree of difficulty is evaluated based on the total number of states. At this time, it is evaluated that the degree of difficulty is high when the total number of states is large, and that the degree of difficulty is low when the total number of states is small. In other words, the degree of difficulty of the diagnosis item increases with an increase in the total number of states branching from the diagnosis item in the diagnosis tree. Stated differently, the degree of difficulty of the diagnosis item increases with an increase in the total number of states that are possible as the state of the diagnosis item. Hereinafter, the details of Step S43 are described with reference to FIG. 18.

In Step S80, the similar diagnosis flow extracting unit 42 reads out the diagnosis tree.

In Step S81, the similar diagnosis flow extracting unit 42 calculates the current diagnosis flow.

In Step S82, the similar diagnosis flow extracting unit 42 counts the total number N of diagnosis items in the read-out diagnosis tree.

In Step S83, the similar diagnosis flow extracting unit 42 counts the total number N of diagnosis items in the read-out diagnosis tree.

In Step S84, the similar diagnosis flow extracting unit 42 calculates the degree of difficulty regarding a current diagnosis item based on the total number N of diagnosis items.

In Step S85, a check is made as to whether or not (i)=N is satisfied, more specifically, whether or not counting of the total number N of diagnosis items is already completed. A transition to End is made when the counting for all the diagnosis items is already completed. A transition to Step S83 is made when the counting for all the diagnosis items is not yet completed, and then the counting of the total number of diagnosis items is continued for the remaining diagnosis item(s).

A consideration is given of a case of calculating the degree of difficulty based on the total number of branches from each diagnosis item in FIG. 3. At this time, the degree of difficulty is determined based only on the total number of branches from the diagnosis item, assuming that the states of the diagnosis items have the same degree of diagnostic difficulty. For example, in FIG. 3, the states below the diagnosis item "Shape" are of the following four kinds: "Irregular", "Polygonal", "Lobular", and "Circular or Elliptical". In comparison, the states below the diagnosis item "Unclear halo (−)" are of the following only two kinds: "Present" and "None". It is evaluated here that determining one of the states "Irregular", "Polygonal", "Lobular", and "Circular or Elliptical" is more difficult than determining one of the states "Present" and "None".

It is to be noted that the degree of difficulty regarding a disease name may be calculated in the same manner. Specifically, the degree of difficulty regarding a disease name may increase with an increase in the total number of disease names derived from the states of each diagnosis item in the diagnosis tree. More specifically, for example in FIG. 3, the degree of difficulty regarding a disease name may increase with an increase in the total number of disease names found in the lowermost blocks in FIG. 3.

(Third Difficulty Pattern: Calculating the Degrees of Difficulty Based on the Likelihoods of Misdiagnoses)

It is to be noted that, in Step S43, the degree of difficulty may be determined for a diagnosis item based on the likelihood of misdiagnosing each disease as another disease. When a large number of misdiagnoses is made regarding a diagnosis item, it is assumed that diagnosing the disease is difficult. For this reason, the degree of difficulty is evaluated based on the likelihood of misdiagnosis. More specifically, the similar diagnosis flow extracting unit 42 calculates the degree of difficulty such that the degree of difficulty increases with an increase in the magnitude of the value that is predetermined for the name of a disease as indicating the likelihood of misdiagnosing the disease as the other disease.

Figure 19:
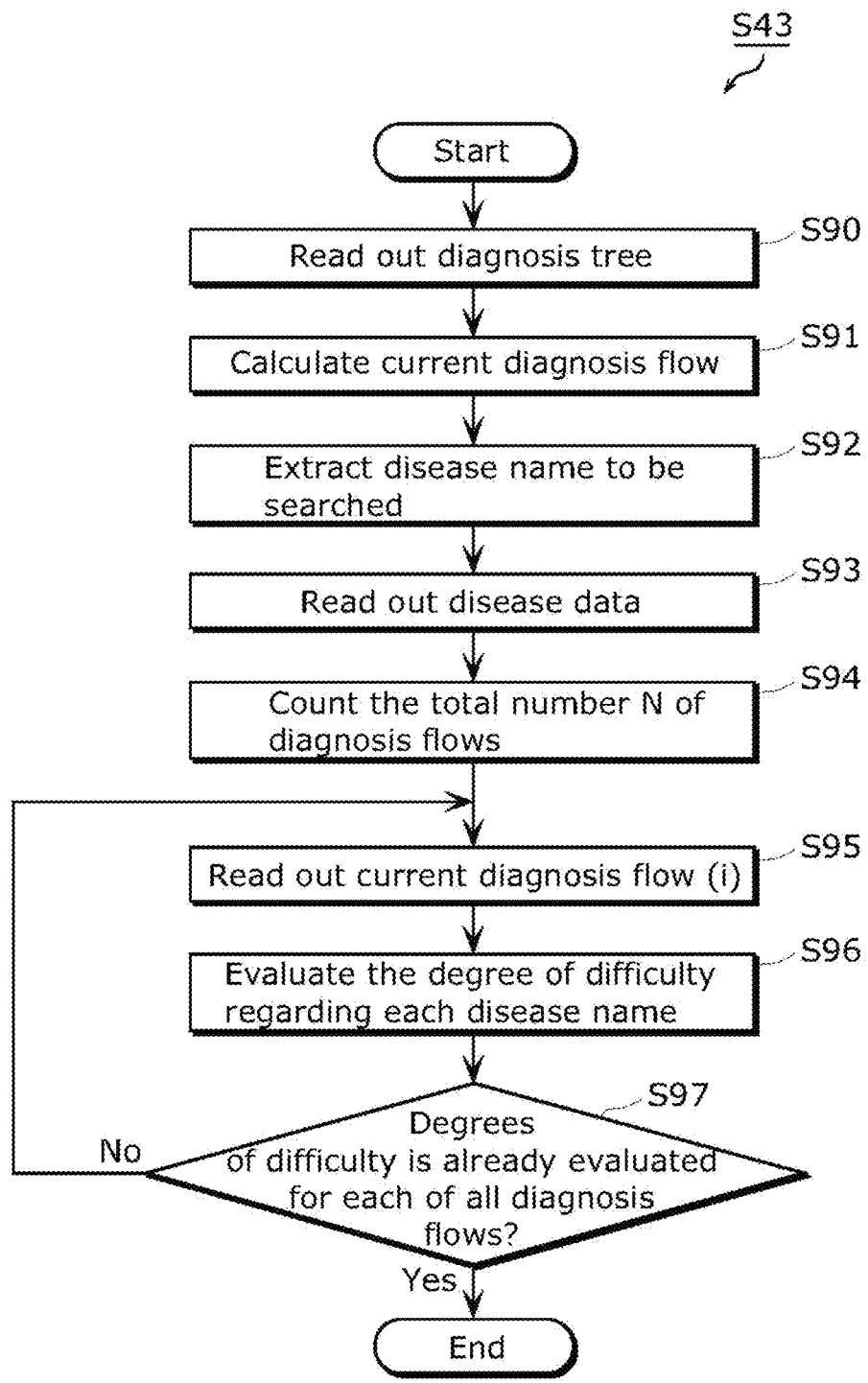
FIG. 19 is a flowchart of processes performed by the similar diagnosis flow extracting unit.

At this time, it is evaluated that the degree of difficulty is high when the likelihood of misdiagnosis is large, and that the degree of difficulty is low when the likelihood of misdiagnosis is small. Hereinafter, the details of Step S43 are described with reference to FIG. 19.

In Step S90, the similar diagnosis flow extracting unit 42 reads out the diagnosis tree.

In Step S91, the similar diagnosis flow extracting unit 42 calculates the current diagnosis flow.

In Step S92, the similar diagnosis flow extracting unit 42 extracts the disease name to be searched.

In Step S93, the similar diagnosis flow extracting unit 42 reads out disease data regarding the disease having the disease name extracted in Step S92 and the disease names in the diagnosis tree.

In Step S94, the similar diagnosis flow extracting unit 42 counts the total number N of diagnosis flows in the read-out diagnosis tree.

In Step S95, the similar diagnosis flow extracting unit 42 reads out a current diagnosis flow (i).

In Step S96, the similar diagnosis flow extracting unit 42 evaluates, based on the disease data, the degree of difficulty regarding each disease name in the current diagnosis flow (i).

In Step S97, a check is made as to whether or not the degree of difficulty regarding disease names is already evaluated for each of all the diagnosis flows. A transition to End is made when the evaluation of all the diagnosis flows is already completed. A transition to Step S95 is made when the evaluation of all the diagnosis flows is not yet completed, and then the evaluation of the degree of difficulty is continued for the remaining diagnosis flow(s).

It is to be noted that, in Step S43, the likelihood of misdiagnosis may be calculated based on the rate of correct diagnosis results that match the results of pathological examinations. Here, the pathological examinations are tests of sampled tumor parts. Such a pathological examination is made on a sampled tumor part at a stage of a medical treatment. Then, a definitive diagnosis is made based not only on the results of image interpretations but also on the results of analyzing the result of the pathological examination. The rate of correct diagnosis results is determined as a matching rate between the result of the pathological examination and the image interpretation results.

It is to be noted that, in Step S43, the degree of difficulty may be calculated by combining the plurality of calculation methods.

A consideration is given of a case of calculating the degree of difficulty based on the likelihood of misdiagnosis in FIG. 3. See the part below the state "Polygonal" to focus on the three possible disease names "Solidtubular carcinoma", "Mucinous carcinoma", and "Medullary carcinoma".

For example, assume that it is difficult to differentiate "Solidtubular carcinoma" and "Medullary carcinoma", but it is easy to differentiate "Solidtubular carcinoma" and "Mucinous carcinoma". Hereinafter, a description is given of a case where the search target disease name is "Solidtubular carcinoma". First, disease data sets are stored in advance. Each disease data set includes the names of diseases such as "Solidtubular carcinoma" and the likelihood of misdiagnosis associated with each other. At the time of search, the disease data regarding "Solidtubular carcinoma" is read out (for example, the disease data indicates that the likelihood of misdiagnosing "Solidtubular carcinoma" as "Mucinous carcinoma" is 0.1, and that the likelihood of misdiagnosing "Solidtubular carcinoma" as "Medullary carcinoma" is 0.7). Here is an exemplary case of performing a search using the character strings "Solidtubular carcinoma" as keywords. In this case, it is possible to increase the degree of similarity of the different character strings such as "Medullary carcinoma" with respect to "Solidtubular carcinoma" by adding the likelihood as the weight for use in the calculation of the degree of similarity with respect to the search target character strings.

(Fourth Difficulty Pattern: Deleting Impossible Diagnosis Flows Based on a Plurality of Diagnosis Trees)

In Step S44, the similar diagnosis flow extracting unit 42 evaluates all combinations of a plurality of diagnosis trees extracted by the diagnosis tree analyzing unit 41, extracts effective similar diagnosis flows while deleting impossible diagnosis flows, and forwards the effective similar diagnosis flows to the similar case search unit 5.

Figure 20:
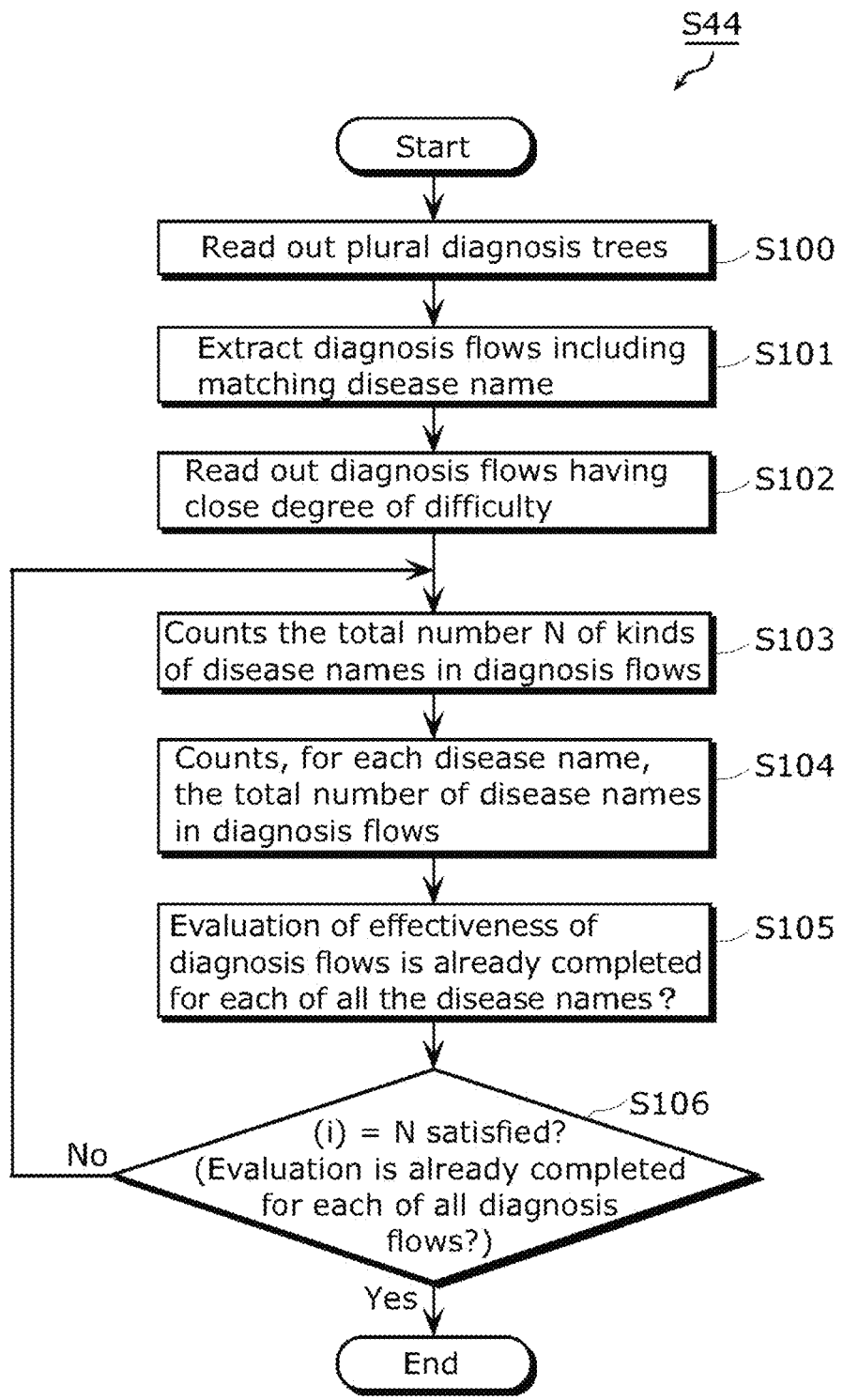
FIG. 20 is a flowchart of processes performed by the similar diagnosis flow extracting unit.

The effective similar diagnosis flows are extracted from among the plurality of diagnosis flows based on an indicator indicating whether or not a given combination of disease names is present in the diagnosis trees. Hereinafter, the details of Step S44 are described with reference to FIG. 20.

In Step S100, the similar diagnosis flow extracting unit 42 reads out the plurality of diagnosis trees.

In Step S101, the similar diagnosis flow extracting unit 42 extracts, from the plurality of diagnosis trees, diagnosis flows including at least one matching disease name also included in the current diagnosis flow.

In Step S102, the similar diagnosis flow extracting unit 42 reads out, from the plurality of diagnosis trees, the extracted similar diagnosis flows including the at least one matching disease name.

In Step S103, the similar diagnosis flow extracting unit 42 counts the total number N of kinds of disease names derived from the diagnosis flows extracted in Steps S101 and S102.

In Step S104, the similar diagnosis flow extracting unit 42 counts, for each disease name, the total number of disease names included in the diagnosis flows in each diagnosis tree.

In Step S105, the similar diagnosis flow extracting unit 42 evaluates and employs, as the effective diagnosis flows, the diagnosis flows that yield the disease names counted in all the diagnosis trees.

In Step S106, an evaluation is made as to whether or not (i)=N is satisfied, more specifically, whether or not such evaluation is already completed for each of all the disease names. A transition is made to End when the evaluation is already completed for each of all the disease names. A transition to Step S103 is made when the evaluation is not yet completed for each of all the disease names, and the evaluation of the remaining disease name(s) is continued.

(Fifth Difficulty Pattern: Changing Targets to be Displayed Based on a Plurality of Diagnosis Trees and a Current Image Interpretation Report)

Figure 21:
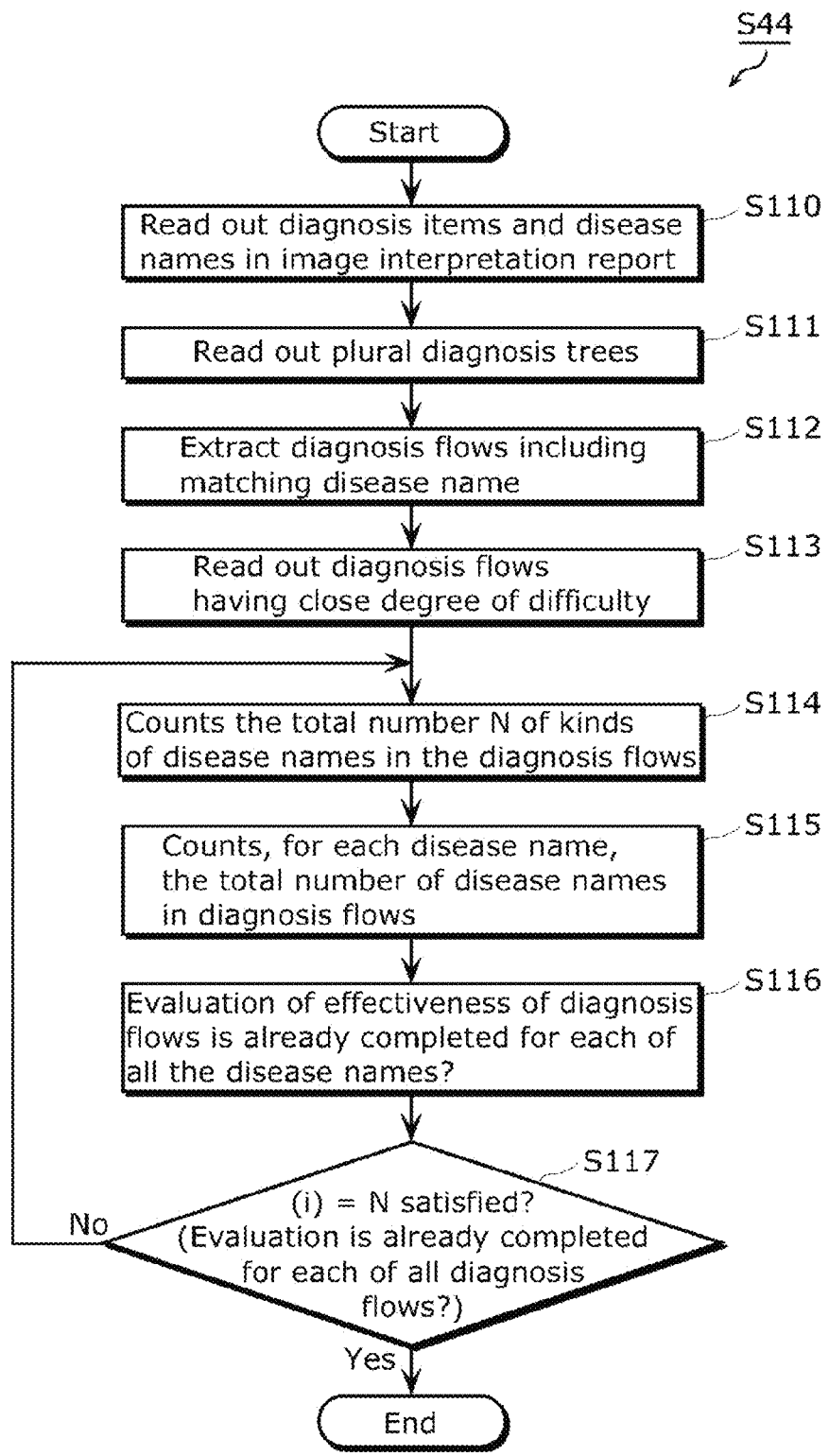
FIG. 21 is a flowchart of processes performed by the similar diagnosis flow extracting unit.

It is to be noted that, in Step S44, diagnosis trees for use may be changed based on diagnosis items included in the current image interpretation report. Here, a description is given of an example of changing diagnosis trees according to the above-described effective diagnosis flow extraction method. Hereinafter, a flow for changing diagnosis trees for use in Step S44 is described in detail with reference to FIG. 21.

In Step S110, the similar diagnosis flow extracting unit 42 reads out the diagnosis items and the disease names included in the current image interpretation report.

In Step S111, the similar diagnosis flow extracting unit 42 selects and reads out the diagnosis trees including the diagnosis items extracted in Step S110.

In Step S112, the similar diagnosis flow extracting unit 42 extracts, from the plurality of diagnosis trees, the diagnosis flows including at least one matching disease name also included in the current diagnosis flow.

In Step S113, the similar diagnosis flow extracting unit 42 reads out, from the plurality of diagnosis trees, the extracted similar diagnosis flows including the at least one matching disease name.

In Step S114, the similar diagnosis flow extracting unit 42 counts the total number N of kinds of disease names included in the diagnosis flows extracted in Steps S112 and S113.

In Step S115, the similar diagnosis flow extracting unit 42 counts, for each disease name, the total number of disease names derived from the diagnosis flows in each diagnosis tree.

In Step S116, the similar diagnosis flow extracting unit 42 employs, as the effective diagnosis flows, the diagnosis flows that yield the disease names counted in all the diagnosis trees.

Figure 22:
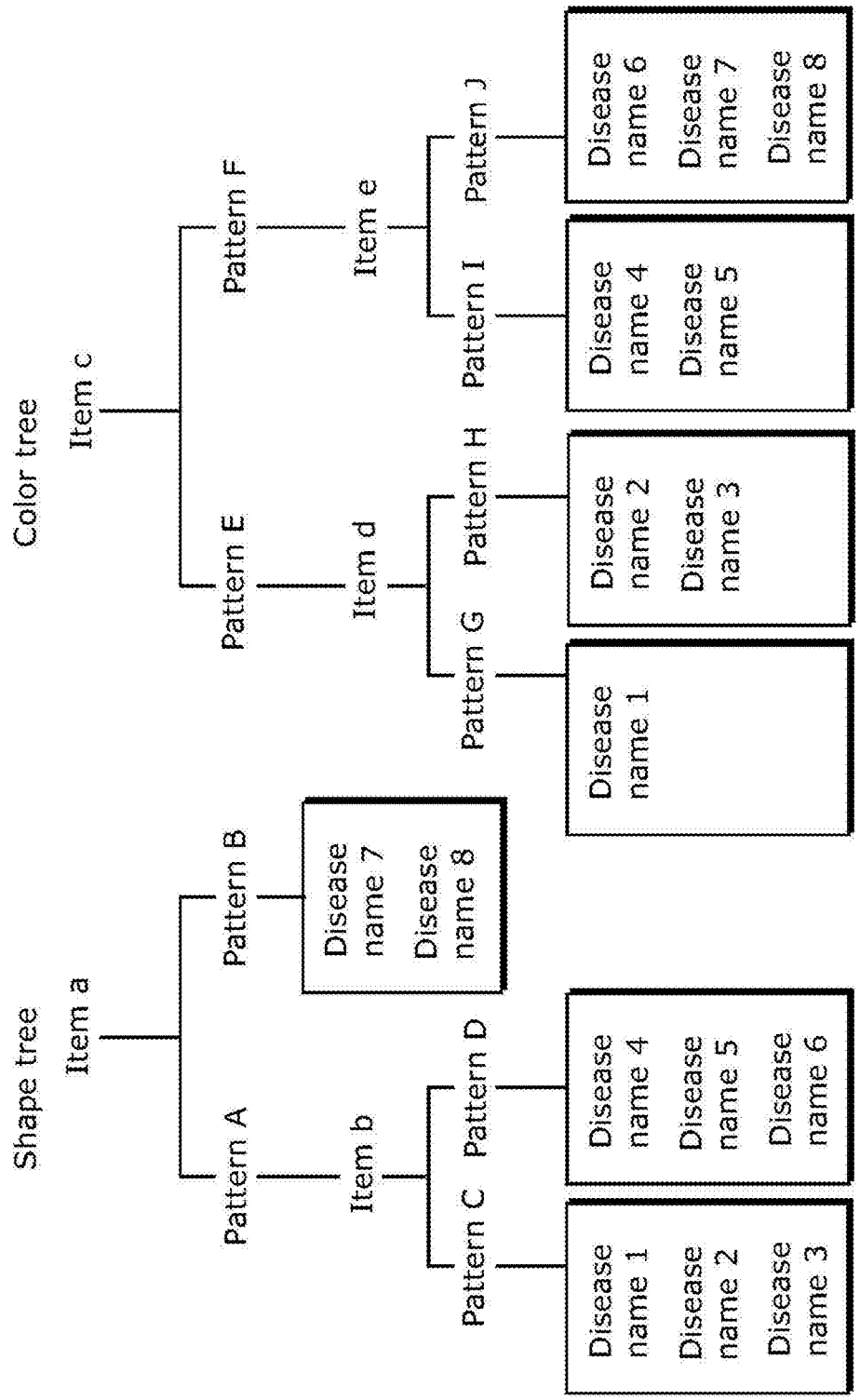
FIG. 22 shows diagnosis trees for explaining how to modify a plurality of diagnosis trees.

In Step S117, an evaluation is made as to whether or not (i)=N is satisfied, more specifically, whether or not such evaluation is already completed for each of all the disease names. A transition is made to End when the evaluation is already completed for each of all the disease names. A transition to Step S114 is made when the evaluation is not yet completed for each of all the disease names, and the evaluation of the remaining disease name(s) is continued. Here is an example case where a plurality of diagnosis trees is present as shown in FIG. 22. It is assumed that a doctor is currently diagnosing based on the shapes of diagnosis items, and that the current diagnosis flow is "from Item a, via Pattern A, Item b, and Pattern B, to Disease 2" in this listed order. It is also assumed that it is difficult to differentiate Diseases 1, 2, and 3 in the diagnosis tree of shapes, and that it is difficult to differentiate Diseases 2 and 3 in the diagnosis tree of colors. In Step S111, the current diagnosis flow in use is read out. In Step 112, the following diagnosis flow is read out: the diagnosis flow "from Item c, via Pattern E, Item d, and Pattern G, to Disease 2" proceeding in this listed order (in the diagnosis tree of colors here) including the disease name also included in the current diagnosis flow. In Step S113, the following similar diagnosis flows in the diagnosis trees are read out: the diagnosis flow "from Item a, vie Pattern A, Item b, and Pattern C, to Disease 1" proceeding in this listed order; the diagnosis flow "from Item a, via Pattern A, Item b, and Pattern C, to Disease 3" proceeding in this listed order; and the diagnosis flow "from Item c, via Pattern E, Item d, and Pattern G, to Disease 3" proceeding in this listed order. To sum up, the following diagnosis flows are read out here.

Diagnosis flow 1: "from Item a, via Pattern A, Item b, and Pattern C, to Disease 1" in this listed order (Diagnosis tree: Shape tree)

Diagnosis flow 2: "from Item a, via Pattern A, Item b, and Pattern C, to Disease 2" in this listed order (Diagnosis tree: Shape tree)

Diagnosis flow 3: "from Item a, via Pattern A, Item b, and Pattern C, to Disease 3" in this listed order (Diagnosis tree: Shape tree)

Diagnosis flow 4: "from Item c, via Pattern E, Item d, and Pattern G, to Disease 2" in this listed order (Diagnosis tree: Color tree)

Diagnosis flow 5: "from Item c, via Pattern E, Item d, and Pattern G, to Disease 3" in this listed order (Diagnosis tree: Color tree)

In other words, when at least two current diagnosis flows included in mutually different diagnosis trees are used, the similar diagnosis flow extracting unit 42 extracts similar diagnosis flows for each of the current diagnosis trees.

As for the diagnosis flows, in Steps S114 and S115, the total number of disease names is counted for each of the shape tree and the color tree. For example, if Disease name 1 were included only in the shape tree, it is possible to exclude it from the targets to be displayed. In this way, it is possible to narrow down the display targets according to such evaluation using in combination the plurality of diagnosis trees.

(S45: Extraction of Similar Diagnosis Flows)

In Step S45, based on the degrees of difficulty, the similar diagnosis flow extracting unit 42 forwards, to the similar case search unit 5, the similar diagnosis flows similar in the degrees of difficulty to the current diagnosis flow. More specifically, the similar diagnosis flow extracting unit 42 extracts the similar diagnosis flows such that diagnosis flows including diagnosis items or disease names having a higher degree of difficulty are more likely to be extracted as the similar diagnosis flows.

(S13: Similar Case Search)

Figure 23:
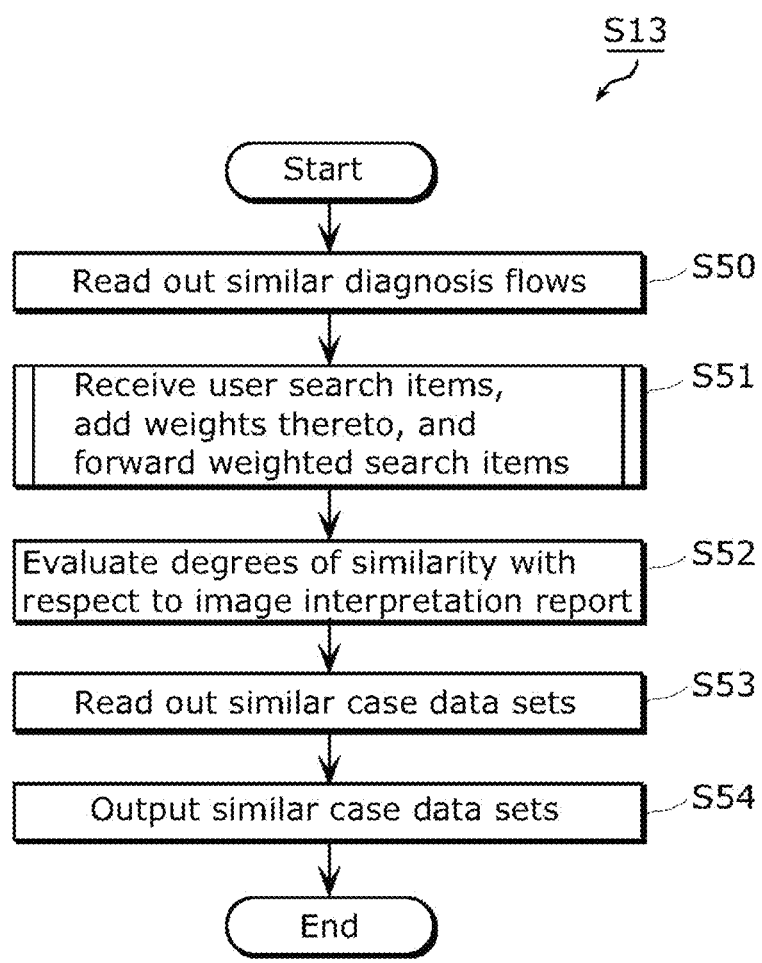
FIG. 23 is a flowchart of processes performed by the similar case search unit.

In Step S13, the similar case search unit 5 receives similar diagnosis flows from the difficulty evaluating unit 4, calculates the degrees of similarity of the respective case data sets stored in the case data storage unit 9, and preferentially forwards case data sets having a higher degree of similarity to the similar case display unit 6. Hereinafter, the details of Step S13 are described with reference to FIG. 23.

In Step S50, the similar case search unit 5 reads out the similar diagnosis flows received from the difficulty evaluating unit 4.

Figure 24:
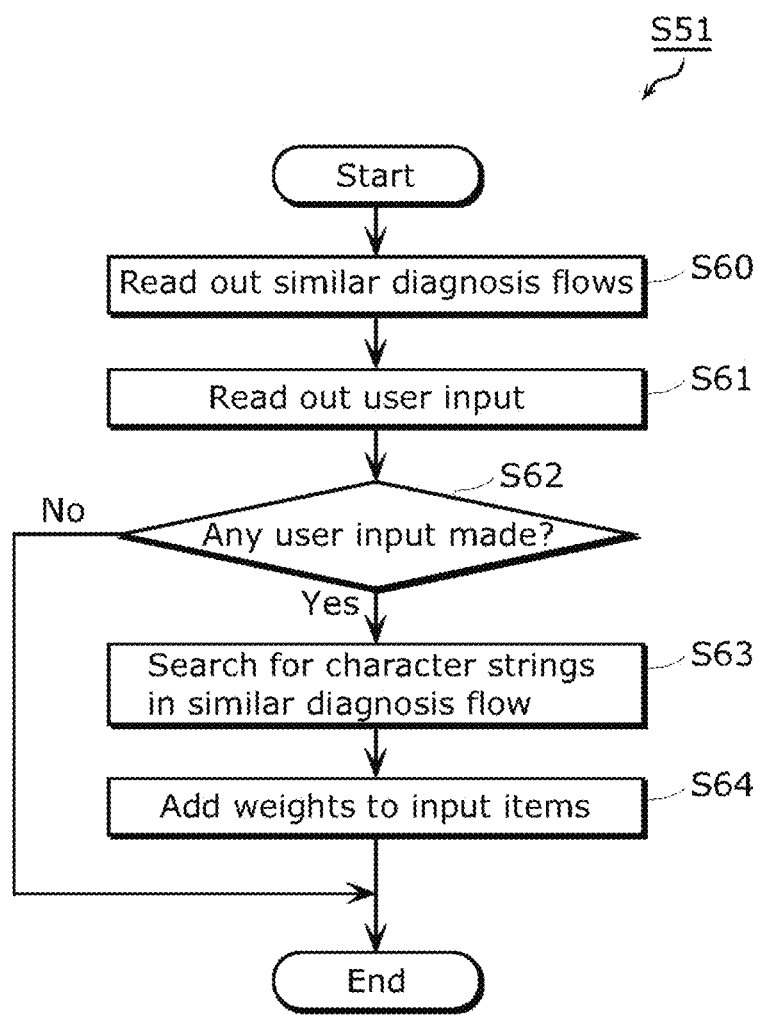
FIG. 24 is a flowchart of processes performed by a search case control unit.

In Step S51, the search case control unit 51 receives search items (character strings) from the input unit 2, adds weights to the search items, and forwards the similar diagnosis flows including the weighted search items to the similarity evaluating unit 52. Hereinafter, the details of Step S51 are described with reference to FIG. 24.

In Step S60, the search case control unit 51 receives the similar diagnosis flows.

In Step S61, the search case control unit 51 reads out the user input through the input unit 2.

In Step S62, a determination is made as to whether or not any user input is made through the input unit 2. When the input is made, a transition to Step S63 is made, and otherwise, a transition to Step S52 is made.

In Step S63, the search case control unit 51 searches the similar diagnosis flows to check whether the character strings input by the user are present or not and, if any, to determine the positions of the character strings.

In Step S64, the search case control unit 51 adds weights to the search items in the diagnosis flow input by the user. This weighting allows the user to preferentially search out desired items. A method of calculating weights is described specifically in Example provided later.

In Step S52, the similarity evaluating unit 52 receives the search items input by the user and the similar diagnosis flows, and evaluates the degrees of similarity to the image interpretation reports stored in the case data storage unit 9.

In Step S53, the similarity evaluating unit 52 reads out, from the case data storage unit 9, the image interpretation reports and medical images included in the case data sets each evaluated in Step S52 as having a high-ranked degree(s) of similarity.

In Step S54, the similarity evaluating unit 52 forwards, to the similar case display unit 6, the image interpretation reports and medical images included in the case data sets read out from the case data storage unit 9.

(S14: Similar Case Display)

In Step S14, the similar case display unit 6 receives the case data sets from the similar case search unit 5, and presents the case data sets to the doctor. The similar case display unit 6 is, for example, a display, a television set, a monitor, or the like.

As described above, the similar case search system 100 according to this embodiment makes it possible to search out case data using similar diagnosis flows extracted based on the degrees of diagnostic difficulty. Accordingly, it is possible to effectively search for case data sets focusing on the diagnosis items or disease names having the high degrees of difficulty, and to thereby search out appropriate case data sets.

EXAMPLE

Figure 25:
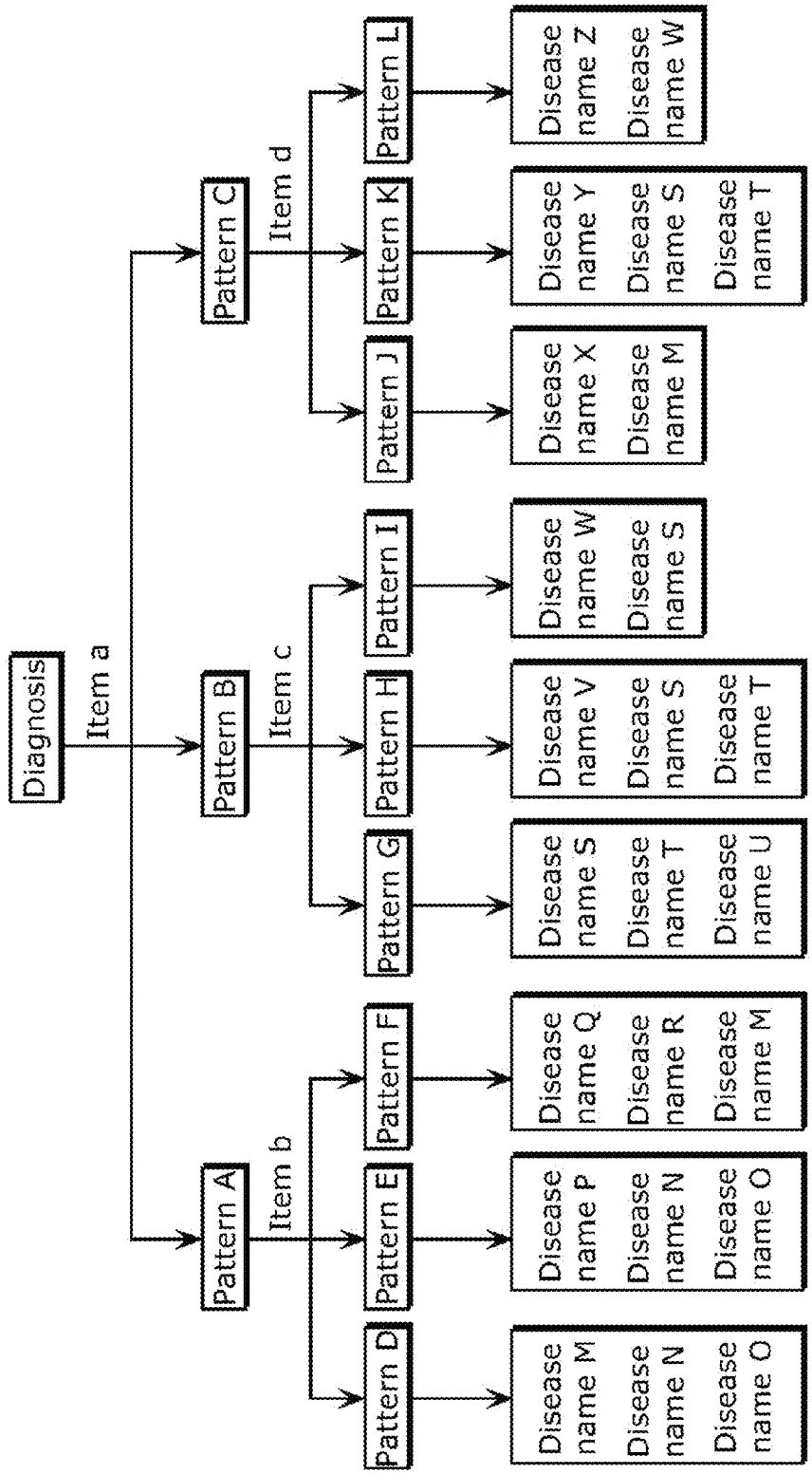
FIG. 25 shows a diagnosis tree used in a similar case search experiment.

Hereinafter, an example is described in which a simple image interpretation report was generated and the degrees of similarity were evaluated. FIG. 25 shows a diagnosis tree used in this example. In FIG. 25, diagnosis items are shown as Items and the states of the diagnosis items are shown as Patterns each enclosed in a block. This diagnosis tree used includes some disease names each commonly included in some of a plurality of diagnosis flows (for example, Disease name N is derived from both of Patterns D and E). In this experiment, it is assumed that the image interpretation report includes the description that "Item a has Pattern B. Item c has Patten G. Disease S is suspected.", and that the following keywords are extracted.

(1) Diagnosis items: "Item a" and "Item c"
(2) States: "Pattern B" and "Pattern G"
(3) Disease name: "Disease S"

In this experiment, the degrees of diagnostic difficulty were evaluated using two difficulty evaluation methods (based on the numbers of disease names commonly derived according to a plurality of diagnosis flows and the likelihoods of misdiagnoses). The evaluation results are shown below. Furthermore, this example was compared with the conventional method for calculating the degrees of similarity based on the indicators that are the numbers of matching character strings. The approach and evaluation equations used at that time are shown below. The degree of similarity Sim was calculated according to the following Equation (1).

[Math. 1]

$$Sim = \frac{\sum_{k=1}^{N} w_k f_k(w, x)}{N} (k = 1, \ldots, N)$$

Expression 1

Here, x denotes the result of comparison between character strings. 1 is taken when the character strings match, and 0 is taken when the character strings do not match. In addition, $f_k$ (w, x) is a function for determining whether or not to perform weighting. Here, 0 is taken when both x and w are 0, and otherwise, 1 is taken.

(1) Conventional Method Approach Based on Indicators that are the Numbers of Matching Character Strings without Performing Difficulty Evaluation)
(Weight: Conventional Method)
[Math. 2]

$$w_k = 1.0$$

Expression 2

(2) Degrees of Difficulty Based on the Numbers of Matching Disease Names

In this experiment, in order to simplify the results, Equation 3 was used for Patterns D to L in FIG. 25 which are the diagnosis results most closer to the disease names among the tree elements below item a. It is to be noted that this calculation may be applied to Patterns A to C by returning back to Item a. Here, $n_x$ denotes the total number of matching disease names included below comparison target branches, and $n_{all}$ denotes the total number of disease names below the comparison target branches. For example, when Pattern D and Pattern E are compared with each other, Disease names M, N, and O are present below Patten D, and Disease names P, N, and O are present below Pattern E. In this case, $n_x$ denotes 2 because Disease names N and O are matching disease names, and the total number $n_{all}$ is 6. Thus, the weight $w_k$ is 0.33.

(Weight: the Total Number of Matching Disease Names)

[Math. 3]

$$w_k = \frac{n_x}{n_{all}}$$

Expression 3

(3) The Degrees of Difficulty Based on the Likelihoods of Misdiagnoses

In this experiment, the disease named as S was most likely to be misdiagnosed, and the disease named as T is second likely to be misdiagnosed. In addition, the numerical value indicating the likelihood of misdiagnosing each disease was calculated according to Equation (4). This numerical value may be determined in advance for each disease or determined automatically with reference to a database.

(Weight: the Likelihood of Misdiagnosis)
[Math. 4]

$$w_k = 1.0 \text{ (Disease name } S\text{)}$$

$$w^k = 0.7 \text{ (Disease name } T\text{)}$$

$$w_k = 0 \text{ (Diseases other than Disease names } S \text{ and } T\text{)}$$

Expression 4

(The Degree of Similarity: Equation (3) is Used)

(4) A Combination of the Degree of Difficulty in (2) and the Degree of Difficulty in (3)

FIG. 26 to FIG. 29 show the results of experiments. Each of the drawings is an association table of diagnosis items in diagnosis flows and the first to tenth degrees of similarity of the diagnosis items. Here, Diagnosis item 1 is a hierarchical layer in which Diagnosis item a is included, and State 1 is the state of Item a. State 1 corresponds to Patterns A, B, or C. Diagnosis item 2 is a hierarchical layer that is positioned below State 1 and in which Items b, c, and d are included. State 2 shows the state of Item b, c, or d. Hereinafter, a current diagnosis flow is shown as "Diagnosis item 1-State 1-Diagnosis item 2-State 2-Disease name". In this notation, the diagnosis flow in a current image interpretation report is symbolized as "a-B-c-G-S".

(1) Conventional Method (Approach Using Indicators that are the Numbers of Matching Character Strings without Performing Difficulty Evaluation)

FIG. 26 shows the result of this experiment. Here, the numbers of matching character strings are used as indicators. With respect to the diagnosis flow "a-B-c-G-S" in the current image interpretation report, the completely matching character string "a-B-c-G-S" has the highest degree of similarity that is shown as 1. The degree of similarity of "a-B-c-G-T" having four matching characters among the five characters is 0.8. In this way, it is possible to search out case data including the same diagnosis flow searched out according to the conventional method.

(2) Degrees of Difficulty Based on the Numbers of Matching Disease Names

FIG. 27 shows the result of this experiment for evaluating the degrees of difficulty based on the numbers of matching disease names. The degrees of difficulty were evaluated based on the indicators that are the numbers of matching disease names. In the case of "Disease name S" in the current image interpretation report, the total number of "Disease name S" in the diagnosis flows is calculated. Based on the calculation result, the degrees of similarity of the diagnosis flows including Disease name S are increased. For example, in FIG. 27, "a-B-c-H-S" and "a-B-c-I-S" are increased from 0.8 to 0.9. For this reason, according to this approach, it is possible to preferentially search out the diagnosis flows that yield the search target disease name. In other words, the diagnosis flows including "Disease name S" that is a disease name having a high degree of difficulty are extracted as the similar diagnosis flows.

(3) The Degrees of Difficulty Based on the Likelihoods of Misdiagnoses

FIG. 28 shows the result of this experiment for evaluating the degrees of difficulty based on the likelihoods of misdiagnoses. When the degrees of difficulty were evaluated based on the indicators that are the likelihoods of misdiagnoses, an increase was found in the degrees of similarity of the diagnosis flows that include the same diagnosis item, state, and "Disease name T" as those in the diagnosis flows including "Disease name S" included in the current image interpretation report. For this reason, this approach makes it possible to preferentially search out the diagnosis flows including the disease names of the diseases likely to be misdiagnosed. In other words, the diagnosis flows including the disease names included in the current diagnosis flow and the disease names of the diseases likely to be misdiagnosed are extracted as the similar diagnosis flows.

(4) A Combination of the Degrees of Difficulty in (2) and the Degrees of Difficulty in (3)

FIG. 29 shows the result of this experiment for evaluating the degrees of difficulty based on the degrees of difficulty in (2) and the degrees of difficulty in (3) used in combination. When the degrees of difficulty are evaluated based on the numbers of matching disease names and the likelihoods of misdiagnoses, the degrees of similarity of some of the diagnosis flows were increased significantly even when the numbers of matching character strings are small. For example, the degree of similarity of the character string "a-B-c-H-T" is 0.6 when the total number of matching characters is counted according to the conventional method but increases to 0.9 when counted according to this proposed approach. Accordingly, this approach makes it possible to lead to the search target disease name and search out preferentially the diagnosis flows including the disease name of the disease likely to be misdiagnosed.

As described above, the above-described similar case search system makes it possible to present not only the case data including similar character strings but also the case data of cases that are difficult to differentiate from the case in the current image interpretation report.

For example, when the current image interpretation report includes the description that "The border part is clear and smooth, and the shape of the border part is polygonal. Thus, Solidtubular carcinoma is suspected.", one of possible diagnosis trees is the diagnosis tree as shown in FIG. 3.

At this time, the above-described keyword extracting unit extracts, from the image interpretation report, the items such as "Border part", "Clear and smooth", "Shape", "Polygonal", and "Solidtubular carcinoma". Next, the keyword extracting unit selects, as the search target, the matching diagnosis flow "Border part-Clear and smooth-Shape-Polygonal-Solidtubular carcinoma" in the diagnosis tree.

The "Irregular" and "Polygonal" were assumed to be confusing. In addition, it was assumed to be difficult to differentiate "Papillotubular carcinoma" and "Solidtubular carcinoma", but it was assumed to be easy to differentiate "Solidtubular carcinoma" and "Mucinous carcinoma". At that time, it was assumed that a database stores past case reports that are Past case 1 "The border part is clear and smooth, and the shape of the border part is polygonal. Thus, Mucinous carcinoma is suspected." and Past case 2 "The border part is clear and smooth, and the shape of the border part is irregular. Thus, Papillotubular carcinoma is suspected.". A doctor can easily differentiate "Solidtubular carcinoma" and "Mucinous carcinoma", and thus Past case 1 does not help the doctor even when presented as the search result.

However, since the conventional approach uses, as indicators, information indicating the matching degrees between the character strings, Past case 1 having a larger number of matching character strings is output as the similar case preferentially over Past case 2. This is because comparison between Past case 1 and Past case 2 shows that Past case 1 includes four matching character strings that are "Border part", "Clear and smooth", "Shape", and "Polygonal" while Past case 2 includes three matching character strings that are "Border part", "Clear and smooth", and "Shape".

In contrast, since the present embodiment calculates and adds weights to "Polygonal" and "Solidtubular carcinoma" that are not included as the search target character strings and uses, as indicators, not only the numbers of matching character strings but also the degrees of difficulty, and thereby increases the degrees of difficulty. As a result, Past case 2 is presented as the search result. In comparison with this confusing case, the doctor can diagnose.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the image decoding apparatus according to each of the embodiments is a program described below.

The program causes a computer to execute a similar case search method including: extracting a keyword from an image interpretation report that is document data including a diagnosis item and a diagnosis result, the diagnosis item being a diagnosis target in interpretation of a medical image, and the diagnosis result showing a state of the diagnosis item; extracting, based on the keyword, one or more target diagnosis flows corresponding to the image interpretation report, by referring to a diagnosis tree storage unit storing one or more diagnosis trees each of which includes a plurality of diagnosis flows each including a diagnosis item and a state of the diagnosis item which are used to determine a disease name; extracting one or more similar diagnosis flows similar to the one or more target diagnosis flows from among the plurality of diagnosis flows included in the diagnosis trees stored in the diagnosis tree storage unit, based on a degree of difficulty regarding a diagnosis item or a degree of difficulty regarding a disease name, the degree of difficulty regarding a diagnosis item being a degree of difficulty in determining a state of a diagnosis item, and the degree of difficulty regarding a disease name being a degree of difficulty in determining a disease name; and searching out one or more case data sets corresponding to the one or more similar diagnosis flows from among a plurality of case data sets stored in a case data storage unit.

A similar case search apparatus 1 according to an aspect of the present disclosure has been described above based on the non-limiting and exemplary embodiment. The herein disclosed subject matter is to be considered descriptive and illustrative only, and the appended claims are of a scope intended to cover and encompass not only the particular embodiment(s) disclosed, but also equivalent structures, methods, and/or uses.

For example, the input unit 2 may receive inputs from a doctor through a user interface for allowing the doctor to select diagnosis items and the states of the diagnosis items prepared in advance.

The input unit 2 may provide the user interface based on data stored in the case data storage unit 9.

It is to be noted that the character string analyzing unit 31 may use a general keyword extraction method (such as keyword extraction based on morpheme analysis and keyword extraction based on N-gram).

The character string comparing unit 32 may make comparison with keywords using a synonym dictionary.

The character string comparing unit 32 may perform conversion for using the same keywords for evaluating the degrees of difficulty using the synonym dictionary in addition to the comparison with the keywords stored in the keyword dictionary storage unit 7.

The diagnosis tree corresponding to an input image interpretation report may be determined based not only on diagnosis items but also on information about test parts (such as breast and abdominal parts) of a patient.

The keywords stored in the keyword dictionary storage unit 7 may be generated with reference to the image interpretation reports stored in the case data storage unit.

The keywords stored in the keyword dictionary storage unit 7 may be generated based on the Disease Classification Table in the ICD10 (the tenth version of the International Disease Classification).

The diagnosis tree storage unit 8 may generate the keywords with reference to the image interpretation reports in the case database (DB).

The case data storage unit 9 may add the current case after the definitive diagnosis is made.

In the above embodiment, the similar diagnosis flow extracting unit 42 calculates the degrees of difficulty, but the similar diagnosis flow extracting unit 42 does not always need to calculate the degrees of difficulty. For example, the similar diagnosis flow extracting unit 42 may read out the degrees of difficulty stored for each diagnosis item or for each disease name from the diagnosis tree storage unit 8.

A part or all of the structural elements of the similar case search apparatus 1 according to the embodiment may be configured with a single system LSI (Large Scale Integration).

The system-LSI is a super-multi-function LSI manufactured by integrating a plurality of structural units on a single chip, and is specifically a computer system configured to include a microprocessor, a ROM (Read Only Memory), a RAM (Random Access Memory), and so on. The ROM stores a computer program. The system LSI achieves its function through the microprocessor's operations according to the computer program.

Furthermore, System LSI is mentioned here, but there are instances where, due to a difference in the degree of integration, the designations IC, LSI, super LSI, and ultra LSI are used. Furthermore, the means for circuit integration is not limited to an LSI, and implementation with a dedicated circuit or a general-purpose processor is also available. In addition, it is also possible to use a Field Programmable Gate Array (FPGA) that is programmable after the LSI is manufactured, and a reconfigurable processor in which connections and settings of circuit cells within the LSI are reconfigurable.

Furthermore, when a circuit integration technology for replacing LSIs with new circuits appears in the future with advancement in semiconductor technology and derivative other technologies, the circuit integration technology may be naturally used to integrate functional blocks. Application of biotechnology is one such possibility.

A similar case search apparatus including these unique processing units disclosed herein can also be realized as a similar case search method including the steps corresponding to the unique processing units of the similar case search apparatus. In addition, the unique steps of the similar case search method can also be realized as a computer program for causing a computer to execute these unique steps of the similar case search method. Such a computer program can naturally be distributed through computer-readable recording media such as CD-ROMs or the like or via communication networks such as the Internet.

It is to be noted that the above-described embodiment is a non-limiting example.

Industrial Applicability

A similar case search apparatus disclosed here is useful for searching out appropriate case data sets (medical images and image interpretation reports) from among a plurality of case data sets stored in a case data storage unit. The similar case search apparatus is widely applicable in other systems for searching out similar data sets from a database storing text data in association with images and drawings in various fields (such as mechanism design, judicial case search, patent search, etc.) in which tree-structured decision making is available.

The invention claimed is:
1. A similar case search apparatus comprising:
a keyword extracting unit configured to extract a keyword from an image interpretation report that is document data including a diagnosis item and a diagnosis result, the diagnosis item being a diagnosis target in interpretation of a medical image, and the diagnosis result showing a state of the diagnosis item;

a diagnosis tree analyzing unit configured to extract, based on the keyword, one or more target diagnosis flows corresponding to the image interpretation report, by referring to a diagnosis tree storage unit storing one or more diagnosis trees each of which includes a plurality of diagnosis flows each including a diagnosis item and a state of the diagnosis item which are used to determine a disease name;

a similar diagnosis flow extracting unit configured to extract one or more similar diagnosis flows similar to the one or more target diagnosis flows from among the plurality of diagnosis flows included in the diagnosis trees stored in the diagnosis tree storage unit, based on a degree of difficulty regarding a diagnosis item or a degree of difficulty regarding a disease name, the degree of difficulty regarding a diagnosis item being a degree of difficulty in determining a state of a diagnosis item, and the degree of difficulty regarding a disease name being a degree of difficulty in determining a disease name; and a similar case search unit configured to search out one or more case data sets corresponding to the one or more similar diagnosis flows from among a plurality of case data sets stored in a case data storage unit, wherein the degree of difficulty regarding a diagnosis item increases with an increase in a total number of states branching from a diagnosis item in the diagnosis trees.

2. The similar case search apparatus according to claim 1, wherein the degree of difficulty regarding a disease name increases with an increase in a total number of diagnosis flows commonly including a matching disease name in the diagnosis trees.

3. The similar case search apparatus according to claim 1, wherein the degree of difficulty regarding a disease name increases with an increase in a total number of disease names derived from states branching from a diagnosis item in one of the diagnosis trees.

4. The similar case search apparatus according to claim 1, wherein the degree of difficulty regarding a disease name increases with an increase in a value that is preset for a disease name and indicating a likelihood of misdiagnosis.

5. The similar case search apparatus according to claim 1, wherein the similar diagnosis flow extracting unit is configured to extract the one or more similar diagnosis flows for each diagnosis tree, when a total number of the one or more target diagnosis flows extracted is at least two and the at least two target diagnosis flows are included in different diagnosis trees.

6. The similar case search apparatus according to claim 1, wherein the similar diagnosis flow extracting unit is configured to extract the one or more similar diagnosis flows from among the plurality of diagnosis flows in the diagnosis trees stored in the diagnosis tree storage unit such that one or more similar diagnosis flows each having a higher degree of difficulty regarding a diagnosis item or a higher degree of difficulty regarding a disease name are more likely to be extracted as the one or more similar diagnosis flows.

7. A similar case search method comprising:

extracting a keyword from an image interpretation report that is document data including a diagnosis item and a diagnosis result, the diagnosis item being a diagnosis target in interpretation of a medical image, and the diagnosis result showing a state of the diagnosis item;

extracting, based on the keyword, one or more target diagnosis flows corresponding to the image interpretation report, by referring to a diagnosis tree storage unit storing one or more diagnosis trees each of which includes a plurality of diagnosis flows each including a diagnosis item and a state of the diagnosis item which are used to determine a disease name;

extracting one or more similar diagnosis flows similar to the one or more target diagnosis flows from among the plurality of diagnosis flows included in the diagnosis trees stored in the diagnosis tree storage unit, based on a degree of difficulty regarding a diagnosis item or a degree of difficulty regarding a disease name, the degree of difficulty regarding a diagnosis item being a degree of difficulty in determining a state of a diagnosis item, and the degree of difficulty regarding a disease name being a degree of difficulty in determining a disease name; and searching out one or more case data sets corresponding to the one or more similar diagnosis flows from among a plurality of case data sets stored in a case data storage unit, wherein the degree of difficulty regarding a diagnosis item increases with an increase in a total number of states branching from a diagnosis item in the diagnosis trees.

8. A non-transitory computer-readable recording medium for use in a computer, the recording medium having a computer program recorded thereon for causing the computer to execute the similar case search method according to claim 7.

* * * * *